United States Patent [19]
Keating et al.

[11] Patent Number: 5,858,662
[45] Date of Patent: Jan. 12, 1999

[54] DIAGNOSIS OF WILLIAMS SYNDROME AND WILLIAMS SYNDROME COGNITIVE PROFILE BY ANALYSIS OF THE PRESENCE OR ABSENCE OF A LIM-KINASE GENE

[75] Inventors: Mark T. Keating, Salt Lake City, Utah; Colleen A. Morris, Las Vegas, Nev.

[73] Assignees: University of Utah Research Foundation, Salt Lake City, Utah; University and College System of Nevada, Reno, Nev.

[21] Appl. No.: 678,039

[22] Filed: Jul. 10, 1996

Related U.S. Application Data

[63] Continuation-in-part of Ser. No. 474,020, Jun. 7, 1995, which is a continuation of Ser. No. 41,576, Apr. 5, 1993, abandoned.

[51] Int. Cl.[6] .............................. C12Q 1/68; C12P 19/34; C12N 15/00
[52] U.S. Cl. ........................... 435/6; 435/91.1; 435/91.2; 536/23.1; 536/23.5; 536/24.31; 536/24.33; 935/76; 935/77
[58] Field of Search .............................. 435/6, 91.1, 91.2, 435/320.1, 183; 536/23.1, 23.5, 24.31, 24.33; 935/1, 8, 26, 76, 77, 78

[56] References Cited

PUBLICATIONS

Lowery e tal., "Strong Corelation of Elastin Deletions, Detected by Fish, with Williams Syndrome: Evaluation of 235 Patients," American Journal of Genetics, vol. 57, pp. 49–53, 1995.

*Primary Examiner*—Bradley L. Sisson
*Attorney, Agent, or Firm*—Rothwell, Figg, Ernst & Kurz, P.C.

[57] ABSTRACT

Williams syndrome (WS) is a developmental disorder that includes poor visuospatial constructive cognition. This syndrome has been studied to identify genes important for human cognitive development. Two families are described which have a partial WS phenotype; affected members have the specific WS cognitive profile and vascular disease, but lack other WS features. Submicroscopic chromosome 7q11.23 deletions cosegregate with this phenotype in both families. DNA sequence analyses of the region affected by the smallest (83.6 kb) deletion revealed two genes, elastin (ELN) and LIM-kinasel (LIMK1). The latter encodes a novel protein kinase with LIM domains and is strongly expressed in the brain. Because ELN mutations cause vascular disease but not cognitive abnormalities, these data implicate LIMK1 hemizygosity in impaired visuospatial constructive cognition.

15 Claims, 8 Drawing Sheets

```
                                    LIM-1
  1  MRLTLLCCTW REERMGEEGS ELPVCASCGQ RIYDGQYLQA LNADWHADCF RCCDCSASLS   60
                                    LIM-2
 61  HQYYEKDGQL FCKKDYWARY GESCHGCSEQ ITKGLVMVAG ELKYHPECFI CLTCGTFIGD  120
                                              DHR
121  GDTYTLVEHS KLYCGHCYYQ TVVTPVIEQI LPDSPGSHLP HTVTLVSIPA SSHGKRGLSV  180

181  SIDPPHGPPG CGTEHSHTVR VQGVDPGCMS PDVKNSIHVG DRILEINGTP IRNVPLDEID  240
                      PEST
241  LLIQETSRLL QLTLEHDPHD TLGHGLGPET SPLSSPAYTP SGEAGSSARQ KPVLRSCSID  300
                              KINASE SUBDOMAINS → I
301  RSPGAGSLGS PASQRKDLGR SESLRVVCRP HRIFRPSDLI HGEVLGKGCF GQAIKVTHRE  360
         II              III          IV                   V
361  TGEVMVMKEL IRFDEETQRT FLKEVKVMRC LEHPNVLKFI GVLYKDKRLN FITEYIKGGT  420
                                    VI                              VII
421  LRGIIKSMDS QYPWSQRVSF AKDIASGMAY LHSMNIIHRD LNSHNCLVRE NKNVVADFG   480
                 NLS                  VIII                   IX
481  LARLMVDEKT QPEGLRSLKK PDRKKRYTVV GNPYWMAPEM INGRSYDEKV DVFSFGIVLC  540
           X                                        XI
541  EIIGRVNADP DYLPRTMDFG LNVRGFLDRY CPPNCPPSFF PITVRCCDLD PEKRPSFVKL  600

601  EHWLETLRMH LAGHLPLGPQ LEQLDRGFWE TYRRGESGLP AHPEVPD                648
```

FIG. 3A

SEQUENCE LISTING ( 1 ) GENERAL INFORMATION:

( i i i ) NUMBER OF SEQUENCES: 42

( 2 ) INFORMATION FOR SEQ ID NO:1:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Primer sequence"

( x i ) SEQUENCE DESCRIPTION: SEQ ID NO:1:

ATGAGGTTGA CGCTACTTTG TTGC        24

( 2 ) INFORMATION FOR SEQ ID NO:2:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Primer sequence"

( x i ) SEQUENCE DESCRIPTION: SEQ ID NO:2:

TCAGTCGGGG ACCTCAGGGT GGGC　　　　　　　　　　　　　　　　　　24

( 2 ) INFORMATION FOR SEQ ID NO:3:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Primer sequence"

( x i ) SEQUENCE DESCRIPTION: SEQ ID NO:3:

GACTTTGGGC TGGCTCGAGA CATGC　　　　　　　　　　　　　　　　　　25

( 2 ) INFORMATION FOR SEQ ID NO:4:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Primer sequence"

( x i ) SEQUENCE DESCRIPTION: SEQ ID NO:4:

CTCCGGAGCC ATCCACTTGA CTGGC　　　　　　　　　　　　　　　　　　25

( 2 ) INFORMATION FOR SEQ ID NO:5:

( i ) SEQUENCE CHARACTERISTICS:
        ( A ) LENGTH: 10 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:5:

ATGAGGTTGA　　　　　　　　　　　　　　　　　　　　　　　　　　　　10

( 2 ) INFORMATION FOR SEQ ID NO:6:

( i ) SEQUENCE CHARACTERISTICS:
        ( A ) LENGTH: 30 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:6:

GGAGAGGAAG GTGCGCGGGC CGCGGGGCGC                                  30

( 2 ) INFORMATION FOR SEQ ID NO:7:

( i ) SEQUENCE CHARACTERISTICS:
        ( A ) LENGTH: 30 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:7:

ACTCCCTTCC CACCCTGCAG GAAGCGAGTT                                  30

( 2 ) INFORMATION FOR SEQ ID NO:8:

( i ) SEQUENCE CHARACTERISTICS:
        ( A ) LENGTH: 30 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:8:

ACTGCTTCAG GTAGGGTGGG GTGCCCAGGG                                  30

( 2 ) INFORMATION FOR SEQ ID NO:9:

( i ) SEQUENCE CHARACTERISTICS:
        ( A ) LENGTH: 30 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:9:

GCCCGGCCCC TCTCCTGCAG GTGTTGTGAC                                  30

( 2 ) INFORMATION FOR SEQ ID NO:10:

( i ) SEQUENCE CHARACTERISTICS:
        ( A ) LENGTH: 30 base pairs
        ( B ) TYPE: nucleic acid
        ( C ) STRANDEDNESS: double
        ( D ) TOPOLOGY: linear ( i i ) MOLECULE TYPE: DNA (genomic)

(iii) HYPOTHETICAL: NO (iv) ANTI-SENSE: NO (vi) ORIGINAL SOURCE:
  (A) ORGANISM: Homo sapiens (xi) SEQUENCE DESCRIPTION: SEQ ID NO:10:

ACTGGTTATG GTGAGCGCCC CCTGCCTTGC 30

(2) INFORMATION FOR SEQ ID NO:11:

(i) SEQUENCE CHARACTERISTICS:
    (A) LENGTH: 30 base pairs
    (B) TYPE: nucleic acid
    (C) STRANDEDNESS: double
    (D) TOPOLOGY: linear (ii) MOLECULE TYPE: DNA (genomic)

(iii) HYPOTHETICAL: NO (iv) ANTI-SENSE: NO (vi) ORIGINAL SOURCE:
    (A) ORGANISM: Homo sapiens (xi) SEQUENCE DESCRIPTION: SEQ ID NO:11:

CCTCCTCACC CCCGCACCAG GTGGCTGGGG 30

(2) INFORMATION FOR SEQ ID NO:12:

(i) SEQUENCE CHARACTERISTICS:
    (A) LENGTH: 30 base pairs
    (B) TYPE: nucleic acid
    (C) STRANDEDNESS: double
    (D) TOPOLOGY: linear (ii) MOLECULE TYPE: DNA (genomic)

(iii) HYPOTHETICAL: NO (iv) ANTI-SENSE: NO (vi) ORIGINAL SOURCE:
    (A) ORGANISM: Homo sapiens (xi) SEQUENCE DESCRIPTION: SEQ ID NO:12:

AGCTGTACTG GTGAGTGCCT TGGCCCCTCC 30

(2) INFORMATION FOR SEQ ID NO:13:

(i) SEQUENCE CHARACTERISTICS:
    (A) LENGTH: 30 base pairs
    (B) TYPE: nucleic acid
    (C) STRANDEDNESS: double
    (D) TOPOLOGY: linear (ii) MOLECULE TYPE: DNA (genomic)

(iii) HYPOTHETICAL: NO (iv) ANTI-SENSE: NO (vi) ORIGINAL SOURCE:
    (A) ORGANISM: Homo sapiens (xi) SEQUENCE DESCRIPTION: SEQ ID NO:13:

CACCCCGGCG GCTCTTGCAG CGGGCACTGC 30

(2) INFORMATION FOR SEQ ID NO:14:

( i ) SEQUENCE CHARACTERISTICS:
    ( A ) LENGTH: 30 base pairs
    ( B ) TYPE: nucleic acid
    ( C ) STRANDEDNESS: double
    ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Homo sapiens ( x i ) SEQUENCE DESCRIPTION: SEQ ID NO:14:

GCGTCCAGGG GTGAGTGGCC GGCCTGCCGA    30

( 2 ) INFORMATION FOR SEQ ID NO:15:

( i ) SEQUENCE CHARACTERISTICS:
        ( A ) LENGTH: 30 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:15:

GACCCCTGCC TTACCCACAG AGTGGATCCG    30

( 2 ) INFORMATION FOR SEQ ID NO:16:

( i ) SEQUENCE CHARACTERISTICS:
        ( A ) LENGTH: 30 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:16:

CCTGGACGAG GTACGGTCCT GAGTCTGTGG    30

( 2 ) INFORMATION FOR SEQ ID NO:17:

( i ) SEQUENCE CHARACTERISTICS:
        ( A ) LENGTH: 30 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:

( A ) ORGANISM: Homo sapiens ( x i ) SEQUENCE DESCRIPTION: SEQ ID NO:17:

CACATGCCTG CTGTCCCCAG ATTGACCTGC                                    30

( 2 ) INFORMATION FOR SEQ ID NO:18:

( i ) SEQUENCE CHARACTERISTICS:
                ( A ) LENGTH: 30 base pairs
                ( B ) TYPE: nucleic acid
                ( C ) STRANDEDNESS: double
                ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
                ( A ) ORGANISM: Homo sapiens ( x i ) SEQUENCE DESCRIPTION: SEQ ID NO:18:

AACCTGTCTT GTAAGTCAGC CTGCTCCTCG                                    30

( 2 ) INFORMATION FOR SEQ ID NO:19:

( i ) SEQUENCE CHARACTERISTICS:
                ( A ) LENGTH: 30 base pairs
                ( B ) TYPE: nucleic acid
                ( C ) STRANDEDNESS: double
                ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
                ( A ) ORGANISM: Homo sapiens ( x i ) SEQUENCE DESCRIPTION: SEQ ID NO:19:

GCACCATGTG TGCCCCCCAG GAGGAGCTGC                                    30

( 2 ) INFORMATION FOR SEQ ID NO:20:

( i ) SEQUENCE CHARACTERISTICS:
                ( A ) LENGTH: 30 base pairs
                ( B ) TYPE: nucleic acid
                ( C ) STRANDEDNESS: double
                ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
                ( A ) ORGANISM: Homo sapiens ( x i ) SEQUENCE DESCRIPTION: SEQ ID NO:20:

GGCTATCAAG GTACAGAGCA TGCCAGGGTC                                    30

( 2 ) INFORMATION FOR SEQ ID NO:21:

( i ) SEQUENCE CHARACTERISTICS:
                ( A ) LENGTH: 30 base pairs
                ( B ) TYPE: nucleic acid
                ( C ) STRANDEDNESS: double
                ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Homo sapiens ( x i ) SEQUENCE DESCRIPTION: SEQ ID NO:21:

CCTCTGTGTC CCACACGCAG GTGACACACC 30

( 2 ) INFORMATION FOR SEQ ID NO:22:

( i ) SEQUENCE CHARACTERISTICS:
    ( A ) LENGTH: 30 base pairs
    ( B ) TYPE: nucleic acid
    ( C ) STRANDEDNESS: double
    ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Homo sapiens ( x i ) SEQUENCE DESCRIPTION: SEQ ID NO:22:

CCTCAAGGAG GTCAGTGAGC GGAATGCCCT 30

( 2 ) INFORMATION FOR SEQ ID NO:23:

( i ) SEQUENCE CHARACTERISTICS:
    ( A ) LENGTH: 30 base pairs
    ( B ) TYPE: nucleic acid
    ( C ) STRANDEDNESS: double
    ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Homo sapiens ( x i ) SEQUENCE DESCRIPTION: SEQ ID NO:23:

GCCTGTTTGT GCCCCGCCAG GTGAAGGTCA 30

( 2 ) INFORMATION FOR SEQ ID NO:24:

( i ) SEQUENCE CHARACTERISTICS:
    ( A ) LENGTH: 30 base pairs
    ( B ) TYPE: nucleic acid
    ( C ) STRANDEDNESS: double
    ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Homo sapiens ( x i ) SEQUENCE DESCRIPTION: SEQ ID NO:24:

CAAGAGCATG GTGAGTCCTG GGCAGAGCCA 30

(2) INFORMATION FOR SEQ ID NO:25:

(i) SEQUENCE CHARACTERISTICS:
        (A) LENGTH: 30 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (xi) SEQUENCE DESCRIPTION: SEQ ID NO:25:

CCATTCTTTC TCCATCCCAG GACAGCCAGT     30

(2) INFORMATION FOR SEQ ID NO:26:

(i) SEQUENCE CHARACTERISTICS:
        (A) LENGTH: 30 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (xi) SEQUENCE DESCRIPTION: SEQ ID NO:26:

ATCAGGGATG GTGAGTGAGC CGGGTGCTCT     30

(2) INFORMATION FOR SEQ ID NO:27:

(i) SEQUENCE CHARACTERISTICS:
        (A) LENGTH: 30 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (xi) SEQUENCE DESCRIPTION: SEQ ID NO:27:

TCCCGTGTCC CCGTCCCTAG GCCTACCTCC     30

(2) INFORMATION FOR SEQ ID NO:28:

(i) SEQUENCE CHARACTERISTICS:
        (A) LENGTH: 30 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO ( v i ) ORIGINAL SOURCE:
   ( A ) ORGANISM: Homo sapiens ( x i ) SEQUENCE DESCRIPTION: SEQ ID NO:28:

GGTCCGCGAG GTGAGTACCA GGGCCCCACG  30

( 2 ) INFORMATION FOR SEQ ID NO:29:

( i ) SEQUENCE CHARACTERISTICS:
      ( A ) LENGTH: 30 base pairs
      ( B ) TYPE: nucleic acid
      ( C ) STRANDEDNESS: double
      ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
      ( A ) ORGANISM: Homo sapiens ( x i ) SEQUENCE DESCRIPTION: SEQ ID NO:29:

ACCCGGCTTC ACCTTCCCAG AACAAGAATG  30

( 2 ) INFORMATION FOR SEQ ID NO:30:

( i ) SEQUENCE CHARACTERISTICS:
      ( A ) LENGTH: 30 base pairs
      ( B ) TYPE: nucleic acid
      ( C ) STRANDEDNESS: double
      ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
      ( A ) ORGANISM: Homo sapiens ( x i ) SEQUENCE DESCRIPTION: SEQ ID NO:30:

ATGATCAACG GTAGTGGTTC AGCCCTGCCC  30

( 2 ) INFORMATION FOR SEQ ID NO:31:

( i ) SEQUENCE CHARACTERISTICS:
      ( A ) LENGTH: 30 base pairs
      ( B ) TYPE: nucleic acid
      ( C ) STRANDEDNESS: double
      ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
      ( A ) ORGANISM: Homo sapiens ( x i ) SEQUENCE DESCRIPTION: SEQ ID NO:31:

CAGTCGGTCT CTTTATCCAG GCCGCAGCTA  30

( 2 ) INFORMATION FOR SEQ ID NO:32:

( i ) SEQUENCE CHARACTERISTICS:
      ( A ) LENGTH: 30 base pairs
      ( B ) TYPE: nucleic acid (C) STRANDEDNESS: double
(D) TOPOLOGY: linear (i i) MOLECULE TYPE: DNA (genomic)

(i i i) HYPOTHETICAL: NO (i v) ANTI-SENSE: NO (v i) ORIGINAL SOURCE:
 (A) ORGANISM: Homo sapiens (x i) SEQUENCE DESCRIPTION: SEQ ID NO:32:

CCTGTGCGAG GTAGGTCCAG GGTTGGGTAG  30

(2) INFORMATION FOR SEQ ID NO:33:

(i) SEQUENCE CHARACTERISTICS:
 (A) LENGTH: 30 base pairs
 (B) TYPE: nucleic acid
 (C) STRANDEDNESS: double
 (D) TOPOLOGY: linear (i i) MOLECULE TYPE: DNA (genomic)

(i i i) HYPOTHETICAL: NO (i v) ANTI-SENSE: NO (v i) ORIGINAL SOURCE:
 (A) ORGANISM: Homo sapiens (x i) SEQUENCE DESCRIPTION: SEQ ID NO:33:

CCGGGCCTTG TACTGGACAG ATCATCGGGC  30

(2) INFORMATION FOR SEQ ID NO:34:

(i) SEQUENCE CHARACTERISTICS:
 (A) LENGTH: 30 base pairs
 (B) TYPE: nucleic acid
 (C) STRANDEDNESS: double
 (D) TOPOLOGY: linear (i i) MOLECULE TYPE: DNA (genomic)

(i i i) HYPOTHETICAL: NO (i v) ANTI-SENSE: NO (v i) ORIGINAL SOURCE:
 (A) ORGANISM: Homo sapiens (x i) SEQUENCE DESCRIPTION: SEQ ID NO:34:

CCGAGAAGAG GTGAGTGGGG TGGGGCCCTG  30

(2) INFORMATION FOR SEQ ID NO:35:

(i) SEQUENCE CHARACTERISTICS:
 (A) LENGTH: 30 base pairs
 (B) TYPE: nucleic acid
 (C) STRANDEDNESS: double
 (D) TOPOLOGY: linear (i i) MOLECULE TYPE: DNA (genomic)

(i i i) HYPOTHETICAL: NO (i v) ANTI-SENSE: NO (v i) ORIGINAL SOURCE:
 (A) ORGANISM: Homo sapiens (x i) SEQUENCE DESCRIPTION: SEQ ID NO:35:

CCCACCCACC TGTCACCCAG GCCATCCTTT 30

(2) INFORMATION FOR SEQ ID NO:36:

(i) SEQUENCE CHARACTERISTICS:
        (A) LENGTH: 10 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (xi) SEQUENCE DESCRIPTION: SEQ ID NO:36:

CCCCGACTGA 10

(2) INFORMATION FOR SEQ ID NO:37:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer sequence"

(iii) HYPOTHETICAL: NO (iv) ANTI-SENSE: NO (vi) ORIGINAL SOURCE:
        (A) ORGANISM: Homo sapiens (xi) SEQUENCE DESCRIPTION: SEQ ID NO:37:

CCTACCTTTC CTGCTGCAAT 20

(2) INFORMATION FOR SEQ ID NO:38:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer sequence"

(iii) HYPOTHETICAL: NO (iv) ANTI-SENSE: YES (vi) ORIGINAL SOURCE:
        (A) ORGANISM: Homo sapiens (xi) SEQUENCE DESCRIPTION: SEQ ID NO:38:

AAAAGAGGC CGGGTATGGT 20

(2) INFORMATION FOR SEQ ID NO:39:

(i) SEQUENCE CHARACTERISTICS:
        (A) LENGTH: 2427 base pairs
        (B) TYPE: nucleic acid
        (C) STRANDEDNESS: double
        (D) TOPOLOGY: linear (ii) MOLECULE TYPE: cDNA ( i i i ) HYPOTHETICAL: NO ( i v ) ANTI-SENSE: NO ( v i ) ORIGINAL SOURCE:
   ( A ) ORGANISM: Homo sapiens ( i x ) FEATURE:
   ( A ) NAME/KEY: CDS
   ( B ) LOCATION: 49..2424

( x i ) SEQUENCE DESCRIPTION: SEQ ID NO:39:

| | | | | | | | | | | | | | | | | |
|---|---|---|---|---|---|---|---|---|---|---|---|---|---|---|---|---|
| CGGGATAAAA | CGAGGTGCGG | AGAGCGGGCT | GGGGCATTTC | TCCCCGAG | ATG | GCG | GGT | | | | | | | | | 57 |
| | | | | | Met | Ala | Gly | | | | | | | | | |
| | | | | | 1 | | | | | | | | | | | |
| CTG | ACG | GCG | GCG | GCC | CCG | CGG | CCC | GGA | GTC | CTC | CTG | CTC | CTG | CTG | TCC | 105 |
| Leu | Thr | Ala | Ala | Ala | Pro | Arg | Pro | Gly | Val | Leu | Leu | Leu | Leu | Leu | Ser | |
| | 5 | | | | | 10 | | | | | 15 | | | | | |
| ATC | CTC | CAC | CCC | TCT | CGG | CCT | GGA | GGG | GTC | CCT | GGG | GCC | ATT | CCT | GGT | 153 |
| Ile | Leu | His | Pro | Ser | Arg | Pro | Gly | Gly | Val | Pro | Gly | Ala | Ile | Pro | Gly | |
| 20 | | | | | 25 | | | | | 30 | | | | | 35 | |
| GGA | GTT | CCT | GGA | GGA | GTC | TTT | TAT | CCA | GGG | GCT | GGT | CTC | GGA | GCC | CTT | 201 |
| Gly | Val | Pro | Gly | Gly | Val | Phe | Tyr | Pro | Gly | Ala | Gly | Leu | Gly | Ala | Leu | |
| | | | | 40 | | | | | 45 | | | | | 50 | | |
| GGA | GGA | GGA | GCG | CTG | GGG | CCT | GGA | GGC | AAA | CCT | CTT | AAG | CCA | GTT | CCC | 249 |
| Gly | Gly | Gly | Ala | Leu | Gly | Pro | Gly | Gly | Lys | Pro | Leu | Lys | Pro | Val | Pro | |
| | | | 55 | | | | | 60 | | | | | 65 | | | |
| GGA | GGG | CTT | GCG | GGT | GCT | GGC | CTT | GGG | GCA | GGG | CTC | GGC | GCC | TTC | CCC | 297 |
| Gly | Gly | Leu | Ala | Gly | Ala | Gly | Leu | Gly | Ala | Gly | Leu | Gly | Ala | Phe | Pro | |
| | | 70 | | | | | 75 | | | | | 80 | | | | |
| GCA | GTT | ACC | TTT | CCG | GGG | GCT | CTG | GTG | CCT | GGT | GGA | GTG | GCT | GAC | GCT | 345 |
| Ala | Val | Thr | Phe | Pro | Gly | Ala | Leu | Val | Pro | Gly | Gly | Val | Ala | Asp | Ala | |
| | 85 | | | | | 90 | | | | | 95 | | | | | |
| GCT | GCA | GCC | TAT | AAA | GCT | GCT | AAG | GCT | GGC | GCT | GGG | CTT | GGT | GGT | GTC | 393 |
| Ala | Ala | Ala | Tyr | Lys | Ala | Ala | Lys | Ala | Gly | Ala | Gly | Leu | Gly | Gly | Val | |
| 100 | | | | | 105 | | | | | 110 | | | | | 115 | |
| CCA | GGA | GTT | GGT | GGC | TTA | GGA | GTG | TCT | GCA | GGT | GCG | GTG | GTT | CCT | CAG | 441 |
| Pro | Gly | Val | Gly | Gly | Leu | Gly | Val | Ser | Ala | Gly | Ala | Val | Val | Pro | Gln | |
| | | | | 120 | | | | | 125 | | | | | 130 | | |
| CCT | GGA | GCC | GGA | GTG | AAG | CCT | GGG | AAA | GTG | CCG | GGT | GTG | GGG | CTG | CCA | 489 |
| Pro | Gly | Ala | Gly | Val | Lys | Pro | Gly | Lys | Val | Pro | Gly | Val | Gly | Leu | Pro | |
| | | | 135 | | | | | 140 | | | | | 145 | | | |
| GGT | GTA | TAC | CCA | GGT | GGC | GTG | CTC | CCA | GGA | GCT | CGG | TTC | CCC | GGT | GTG | 537 |
| Gly | Val | Tyr | Pro | Gly | Gly | Val | Leu | Pro | Gly | Ala | Arg | Phe | Pro | Gly | Val | |
| | | 150 | | | | | 155 | | | | | 160 | | | | |
| GGG | GTG | CTC | CCT | GGA | GTT | CCC | ACT | GGA | GCA | GGA | GTT | AAG | CCC | AAG | GCT | 585 |
| Gly | Val | Leu | Pro | Gly | Val | Pro | Thr | Gly | Ala | Gly | Val | Lys | Pro | Lys | Ala | |
| | 165 | | | | | 170 | | | | | 175 | | | | | |
| CCA | GGT | GTA | GGT | GGA | GCT | TTT | GCT | GGA | ATC | CCA | GGA | GTT | GGA | CCC | TTT | 633 |
| Pro | Gly | Val | Gly | Gly | Ala | Phe | Ala | Gly | Ile | Pro | Gly | Val | Gly | Pro | Phe | |
| 180 | | | | | 185 | | | | | 190 | | | | | 195 | |
| GGG | GGA | CCG | CAA | CCT | GGA | GTC | CCA | CTG | GGG | TAT | CCC | ATC | AAG | GCC | CCC | 681 |
| Gly | Gly | Pro | Gln | Pro | Gly | Val | Pro | Leu | Gly | Tyr | Pro | Ile | Lys | Ala | Pro | |
| | | | 200 | | | | | 205 | | | | | 210 | | | |
| AAG | CTG | CCT | GGT | GGC | TAT | GGA | CTG | CCC | TAC | ACC | ACA | GGG | AAA | CTG | CCC | 729 |
| Lys | Leu | Pro | Gly | Gly | Tyr | Gly | Leu | Pro | Tyr | Thr | Thr | Gly | Lys | Leu | Pro | |
| | | | 215 | | | | | 220 | | | | | 225 | | | |
| TAT | GGC | TAT | GGG | CCC | GGA | GGA | GTG | GCT | GGT | GCA | GCG | GGC | AAG | GCT | GGT | 777 |
| Tyr | Gly | Tyr | Gly | Pro | Gly | Gly | Val | Ala | Gly | Ala | Ala | Gly | Lys | Ala | Gly | |
| | | 230 | | | | | 235 | | | | | 240 | | | | |
| TAC | CCA | ACA | GGG | ACA | GGG | GTT | GGC | CCC | CAG | GCA | GCA | GCA | GCA | GCG | GCA | 825 |
| Tyr | Pro | Thr | Gly | Thr | Gly | Val | Gly | Pro | Gln | Ala | Ala | Ala | Ala | Ala | Ala | |

```
          245                      250                        255
GCT AAA GCA GCA GCA AAG TTC GGT GCT GGA GCA GCC GGA GTC CTC CCT        873
Ala Lys Ala Ala Ala Lys Phe Gly Ala Gly Ala Ala Gly Val Leu Pro
260             265                 270                 275

GGT GTT GGA GGG GCT GGT GTT CCT GGC GTG CCT GGG GCA ATT CCT GGA        921
Gly Val Gly Gly Ala Gly Val Pro Gly Val Pro Gly Ala Ile Pro Gly
                280                 285                 290

ATT GGA GGC ATC GCA GGT GTT GGG ACT CCA GCT GCA GCT GCA GCT GCA        969
Ile Gly Gly Ile Ala Gly Val Gly Thr Pro Ala Ala Ala Ala Ala Ala
            295                 300                 305

GCA GCA GCC GCT AAG GCA GCC AAG TAT GGA GCT GCT GCA GGC TTA GTG       1017
Ala Ala Ala Ala Lys Ala Ala Lys Tyr Gly Ala Ala Ala Gly Leu Val
        310                 315                 320

CCT GGT GGG CCA GGC TTT GGC CCG GGA GTA GTT GGT GTC CCA GGA GCT       1065
Pro Gly Gly Pro Gly Phe Gly Pro Gly Val Val Gly Val Pro Gly Ala
325                 330                 335

GGC GTT CCA GGT GTT GGT GTC CCA GGA GCT GGG ATT CCA GTT GTC CCA       1113
Gly Val Pro Gly Val Gly Val Pro Gly Ala Gly Ile Pro Val Val Pro
340                 345                 350                 355

GGT GCT GGG ATC CCA GGT GCT GCG GTT CCA GGG GTT GTG TCA CCA GAA       1161
Gly Ala Gly Ile Pro Gly Ala Ala Val Pro Gly Val Val Ser Pro Glu
                360                 365                 370

GCA GCT GCT AAG GCA GCT GCA AAG GCA GCC AAA TAC GGG GCC AGG CCC       1209
Ala Ala Ala Lys Ala Ala Ala Lys Ala Ala Lys Tyr Gly Ala Arg Pro
            375                 380                 385

GGA GTC GGA GTT GGA GGC ATT CCT ACT TAC GGG GTT GGA GCT GGG GGC       1257
Gly Val Gly Val Gly Gly Ile Pro Thr Tyr Gly Val Gly Ala Gly Gly
        390                 395                 400

TTT CCC GGC TTT GGT GTC GGA GTC GGA GGT ATC CCT GGA GTC GCA GGT       1305
Phe Pro Gly Phe Gly Val Gly Val Gly Gly Ile Pro Gly Val Ala Gly
405                 410                 415

GTC CCT AGT GTC GGA GGT GTT CCC GGA GTC GGA GGT GTC CCG GGA GTT       1353
Val Pro Ser Val Gly Gly Val Pro Gly Val Gly Gly Val Pro Gly Val
420                 425                 430                 435

GGC ATT TCC CCC GAA GCT CAG GCA GCA GCT GCC GCC AAG GCT GCC AAG       1401
Gly Ile Ser Pro Glu Ala Gln Ala Ala Ala Ala Lys Ala Ala Lys
                440                 445                 450

TAC GGT GCT GCA GGA GCA GGA GTG CTG GGT GGG CTA GTG CCA GGT CCC       1449
Tyr Gly Ala Ala Gly Ala Gly Val Leu Gly Gly Leu Val Pro Gly Pro
            455                 460                 465

CAG GCG GCA GTC CCA GGT GTG CCG GGC ACG GGA GGA GTG CCA GGA GTG       1497
Gln Ala Ala Val Pro Gly Val Pro Gly Thr Gly Gly Val Pro Gly Val
        470                 475                 480

GGG ACC CCA GCA GCT GCA GCT GCT AAA GCA GCC GCC AAA GCC GCC CAG       1545
Gly Thr Pro Ala Ala Ala Ala Ala Lys Ala Ala Ala Lys Ala Ala Gln
485                 490                 495

TTT GCT CTT CTC AAT CTT GCA GGG TTA GTT CCT GGT GTC GGC GTG GCT       1593
Phe Ala Leu Leu Asn Leu Ala Gly Leu Val Pro Gly Val Gly Val Ala
500                 505                 510                 515

CCT GGA GTT GGC GTG GCT CCT GGT GTC GGT GTG GCT CCT GGA GTT GGC       1641
Pro Gly Val Gly Val Ala Pro Gly Val Gly Val Ala Pro Gly Val Gly
                520                 525                 530

TTG GCT CCT GGA GTT GGC GTG GCT CCT GGA GTT GGT GTG GCT CCT GGC       1689
Leu Ala Pro Gly Val Gly Val Ala Pro Gly Val Gly Val Ala Pro Gly
            535                 540                 545

GTT GGC GTG GCT CCC GGC ATT GGC CCT GGT GGA GTT GCA GCT GCA GCA       1737
Val Gly Val Ala Pro Gly Ile Gly Pro Gly Gly Val Ala Ala Ala Ala
        550                 555                 560

AAA TCC GCT GCC AAG GTG GCT GCC AAA GCC CAG CTC CGA GCT GCA GCT       1785
Lys Ser Ala Ala Lys Val Ala Ala Lys Ala Gln Leu Arg Ala Ala Ala
```

|     |     |     |     |     | 565 |     |     |     |     | 570 |     |     |     |     | 575 |     |      |
|-----|-----|-----|-----|-----|-----|-----|-----|-----|-----|-----|-----|-----|-----|-----|-----|-----|------|
| GGG | CTT | GGT | GCT | GGC | ATC | CCT | GGA | CTT | GGA | GTT | GGT | GTC | GGC | GTC | CCT |     | 1833 |
| Gly | Leu | Gly | Ala | Gly | Ile | Pro | Gly | Leu | Gly | Val | Gly | Val | Gly | Val | Pro |     |      |
| 580 |     |     |     |     | 585 |     |     |     |     | 590 |     |     |     |     | 595 |     |      |

```
GGA CTT GGA GTT GGT GCT GGT GTT CCT GGA CTT GGA GTT GGT GCT GGT                    1881
Gly Leu Gly Val Gly Ala Gly Val Pro Gly Leu Gly Val Gly Ala Gly
                        600                 605                 610

GTT CCT GGC TTC GGG GCA GGT GCA GAT GAG GGA GTT AGG CGG AGC CTG                    1929
Val Pro Gly Phe Gly Ala Gly Ala Asp Glu Gly Val Arg Arg Ser Leu
                615                 620                 625

TCC CCT GAG CTC AGG GAA GGA GAT CCC TCC TCC TCT CAG CAC CTC CCC                    1977
Ser Pro Glu Leu Arg Glu Gly Asp Pro Ser Ser Ser Gln His Leu Pro
        630                 635                 640

AGC ACC CCC TCA TCA CCC AGG GTA CCT GGA GCC CTG GCT GCC GCT AAA                    2025
Ser Thr Pro Ser Ser Pro Arg Val Pro Gly Ala Leu Ala Ala Ala Lys
    645                 650                 655

GCA GCC AAA TAT GGA GCA GCA GTG CCT GGG GTC CTT GGA GGG CTC GGG                    2073
Ala Ala Lys Tyr Gly Ala Ala Val Pro Gly Val Leu Gly Gly Leu Gly
660                 665                 670                 675

GCT CTC GGT GGA GTA GGC ATC CCA GGC GGT GTG GTG GGA GCC GGA CCC                    2121
Ala Leu Gly Gly Val Gly Ile Pro Gly Gly Val Val Gly Ala Gly Pro
                        680                 685                 690

GCC GCC GCC GCT GCC GCA GCC AAA GCT GCT GCC AAA GCC GCC CAG TTT                    2169
Ala Ala Ala Ala Ala Ala Ala Lys Ala Ala Ala Lys Ala Ala Gln Phe
                695                 700                 705

GGC CTA GTG GGA GCC GCT GGG CTC GGA GGA CTC GGA GTC GGA GGG CTT                    2217
Gly Leu Val Gly Ala Ala Gly Leu Gly Gly Leu Gly Val Gly Gly Leu
        710                 715                 720

GGA GTT CCA GGT GTT GGG GGC CTT GGA GGT ATA CCT CCA GCT GCA GCC                    2265
Gly Val Pro Gly Val Gly Gly Leu Gly Gly Ile Pro Pro Ala Ala Ala
    725                 730                 735

GCT AAA GCA GCT AAA TAC GGT GCT GCT GGC CTT GGA GGT GTC CTA GGG                    2313
Ala Lys Ala Ala Lys Tyr Gly Ala Ala Gly Leu Gly Gly Val Leu Gly
740                 745                 750                 755

GGT GCC GGG CAG TTC CCA CTT GGA GGA GTG GCA GCA AGA CCT GGC TTC                    2361
Gly Ala Gly Gln Phe Pro Leu Gly Gly Val Ala Ala Arg Pro Gly Phe
                        760                 765                 770

GGA TTG TCT CCC ATT TTC CCA GGT GGG GCC TGC CTG GGG AAA GCT TGT                    2409
Gly Leu Ser Pro Ile Phe Pro Gly Gly Ala Cys Leu Gly Lys Ala Cys
                775                 780                 785

GGC CGG AAG AGA AAA TGA                                                            2427
Gly Arg Lys Arg Lys
790
```

( 2 ) INFORMATION FOR SEQ ID NO:40:

( i ) SEQUENCE CHARACTERISTICS:
        ( A ) LENGTH: 792 amino acids
        ( B ) TYPE: amino acid
        ( D ) TOPOLOGY: linear ( i i ) MOLECULE TYPE: protein ( x i ) SEQUENCE DESCRIPTION: SEQ ID NO:40:

```
Met Ala Gly Leu Thr Ala Ala Ala Pro Arg Pro Gly Val Leu Leu Leu
 1               5                   10                  15

Leu Leu Ser Ile Leu His Pro Ser Arg Pro Gly Gly Val Pro Gly Ala
                20                  25                  30

Ile Pro Gly Gly Val Pro Gly Gly Val Phe Tyr Pro Gly Ala Gly Leu
                35                  40                  45

Gly Ala Leu Gly Gly Gly Ala Leu Gly Pro Gly Gly Lys Pro Leu Lys
```

-continued

|        | 50  |        |     |     | 55  |     |     |     | 60  |     |     |     |     |     |
|--------|-----|--------|-----|-----|-----|-----|-----|-----|-----|-----|-----|-----|-----|-----|

Pro Val Pro Gly Gly Leu Ala Gly Ala Gly Leu Gly Ala Gly Leu Gly
65                      70                  75                      80

Ala Phe Pro Ala Val Thr Phe Pro Gly Ala Leu Val Pro Gly Gly Val
                    85                  90                      95

Ala Asp Ala Ala Ala Ala Tyr Lys Ala Ala Lys Ala Gly Ala Gly Leu
                100                 105                 110

Gly Gly Val Pro Gly Val Gly Gly Leu Gly Val Ser Ala Gly Ala Val
            115             120                 125

Val Pro Gln Pro Gly Ala Gly Val Lys Pro Gly Lys Val Pro Gly Val
    130                 135                 140

Gly Leu Pro Gly Val Tyr Pro Gly Gly Val Leu Pro Gly Ala Arg Phe
145                 150                 155                     160

Pro Gly Val Gly Val Leu Pro Gly Val Pro Thr Gly Ala Gly Val Lys
                    165             170                     175

Pro Lys Ala Pro Gly Val Gly Gly Ala Phe Ala Gly Ile Pro Gly Val
            180                 185                 190

Gly Pro Phe Gly Gly Pro Gln Pro Gly Val Pro Leu Gly Tyr Pro Ile
        195                 200                 205

Lys Ala Pro Lys Leu Pro Gly Gly Tyr Gly Leu Pro Tyr Thr Thr Gly
210                 215                 220

Lys Leu Pro Tyr Gly Tyr Gly Pro Gly Gly Val Ala Gly Ala Ala Gly
225                 230                 235                     240

Lys Ala Gly Tyr Pro Thr Gly Thr Gly Val Gly Pro Gln Ala Ala Ala
                245                 250                 255

Ala Ala Ala Ala Lys Ala Ala Ala Lys Phe Gly Ala Gly Ala Ala Gly
            260                 265                 270

Val Leu Pro Gly Val Gly Gly Ala Gly Val Pro Gly Val Pro Gly Ala
        275                 280                 285

Ile Pro Gly Ile Gly Gly Ile Ala Gly Val Gly Thr Pro Ala Ala Ala
    290                 295                 300

Ala Ala Ala Ala Ala Ala Ala Lys Ala Ala Lys Tyr Gly Ala Ala Ala
305                 310                 315                     320

Gly Leu Val Pro Gly Gly Pro Gly Phe Gly Pro Gly Val Val Gly Val
                325                 330                 335

Pro Gly Ala Gly Val Pro Gly Val Gly Val Pro Gly Ala Gly Ile Pro
            340                 345                 350

Val Val Pro Gly Ala Gly Ile Pro Gly Ala Ala Val Pro Gly Val Val
        355                 360                 365

Ser Pro Glu Ala Ala Ala Lys Ala Ala Ala Lys Ala Ala Lys Tyr Gly
    370                 375                 380

Ala Arg Pro Gly Val Gly Val Gly Gly Ile Pro Thr Tyr Gly Val Gly
385                 390                 395                     400

Ala Gly Gly Phe Pro Gly Phe Gly Val Gly Val Gly Gly Ile Pro Gly
                405                 410                 415

Val Ala Gly Val Pro Ser Val Gly Gly Val Pro Gly Val Gly Gly Val
            420                 425                 430

Pro Gly Val Gly Ile Ser Pro Glu Ala Gln Ala Ala Ala Ala Ala Lys
        435                 440                 445

Ala Ala Lys Tyr Gly Ala Ala Gly Ala Gly Val Leu Gly Gly Leu Val
    450                 455                 460

Pro Gly Pro Gln Ala Ala Val Pro Gly Val Pro Gly Thr Gly Gly Val
465                 470                 475                 480

| Pro | Gly | Val | Gly | Thr<br>485 | Pro | Ala | Ala | Ala<br>490 | Ala | Lys | Ala | Ala | Ala<br>495 | Lys |
|---|---|---|---|---|---|---|---|---|---|---|---|---|---|---|
| Ala | Ala | Gln | Phe<br>500 | Ala | Leu | Leu | Asn | Leu<br>505 | Ala | Gly | Leu | Val | Pro<br>510 | Gly | Val |
| Gly | Val | Ala<br>515 | Pro | Gly | Val | Gly<br>520 | Val | Ala | Pro | Gly | Val<br>525 | Gly | Val | Ala | Pro |
| Gly | Val<br>530 | Gly | Leu | Ala | Pro | Gly<br>535 | Val | Gly | Val | Ala | Pro<br>540 | Gly | Val | Gly | Val |
| Ala<br>545 | Pro | Gly | Val | Gly | Val<br>550 | Ala | Pro | Gly | Ile | Gly<br>555 | Pro | Gly | Gly | Val | Ala<br>560 |
| Ala | Ala | Ala | Lys | Ser<br>565 | Ala | Ala | Lys | Val<br>570 | Ala | Ala | Lys | Ala | Gln | Leu<br>575 | Arg |
| Ala | Ala | Ala | Gly<br>580 | Leu | Gly | Ala | Gly | Ile<br>585 | Pro | Gly | Leu | Gly | Val<br>590 | Gly | Val |
| Gly | Val | Pro<br>595 | Gly | Leu | Gly | Val | Gly<br>600 | Ala | Gly | Val | Pro | Gly<br>605 | Leu | Gly | Val |
| Gly | Ala<br>610 | Gly | Val | Pro | Gly | Phe<br>615 | Gly | Ala | Gly | Ala | Asp<br>620 | Glu | Gly | Val | Arg |
| Arg<br>625 | Ser | Leu | Ser | Pro | Glu<br>630 | Leu | Arg | Glu | Gly | Asp<br>635 | Pro | Ser | Ser | Ser | Gln<br>640 |
| His | Leu | Pro | Ser | Thr<br>645 | Pro | Ser | Ser | Pro | Arg<br>650 | Val | Pro | Gly | Ala | Leu<br>655 | Ala |
| Ala | Ala | Lys | Ala<br>660 | Ala | Lys | Tyr | Gly | Ala<br>665 | Ala | Val | Pro | Gly | Val<br>670 | Leu | Gly |
| Gly | Leu | Gly<br>675 | Ala | Leu | Gly | Gly | Val<br>680 | Gly | Ile | Pro | Gly | Gly<br>685 | Val | Val | Gly |
| Ala | Gly<br>690 | Pro | Ala | Ala | Ala | Ala<br>695 | Ala | Ala | Lys | Ala<br>700 | Ala | Ala | Lys | Ala |
| Ala<br>705 | Gln | Phe | Gly | Leu | Val<br>710 | Gly | Ala | Ala | Gly | Leu<br>715 | Gly | Gly | Leu | Gly | Val<br>720 |
| Gly | Gly | Leu | Gly | Val<br>725 | Pro | Gly | Val | Gly | Gly<br>730 | Leu | Gly | Gly | Ile | Pro<br>735 | Pro |
| Ala | Ala | Ala | Ala<br>740 | Lys | Ala | Ala | Lys | Tyr<br>745 | Gly | Ala | Ala | Gly | Leu<br>750 | Gly | Gly |
| Val | Leu | Gly<br>755 | Gly | Ala | Gly | Gln | Phe<br>760 | Pro | Leu | Gly | Gly | Val<br>765 | Ala | Ala | Arg |
| Pro | Gly<br>770 | Phe | Gly | Leu | Ser | Pro<br>775 | Ile | Phe | Pro | Gly | Gly<br>780 | Ala | Cys | Leu | Gly |
| Lys<br>785 | Ala | Cys | Gly | Arg | Lys<br>790 | Arg | Lys |

( 2 ) INFORMATION FOR SEQ ID NO:41:

( i ) SEQUENCE CHARACTERISTICS:
        ( A ) LENGTH: 3262 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Homo sapiens ( i x ) FEATURE:
        ( A ) NAME/KEY: CDS ( B ) LOCATION: 96..2036

( x i ) SEQUENCE DESCRIPTION: SEQ ID NO:41:

```
GCGCCGAGCC GGTTTCCCCG CCGGTGTCCG AGAGGCGCCC CCGGCCCGGC CGCCCCCAGC        60

CCCAGCCCCG CCGGGCCCCG CCCCCCGTCG AGTGC ATG AGG TTG ACG CTA CTT          113
                                       Met Arg Leu Thr Leu Leu
                                         1               5

TGT TGC ACC TGG AGG GAA GAA CGT ATG GGA GAG GAA GGA AGC GAG TTG         161
Cys Cys Thr Trp Arg Glu Glu Arg Met Gly Glu Glu Gly Ser Glu Leu
         10                  15                  20

CCC GTG TGT GCA AGC TGC GGC CAG AGG ATC TAT GAT GGC CAG TAC CTC         209
Pro Val Cys Ala Ser Cys Gly Gln Arg Ile Tyr Asp Gly Gln Tyr Leu
             25                  30                  35

CAG GCC CTG AAC GCG GAC TGG CAC GCA GAC TGC TTC AGG TGT TGT GAC         257
Gln Ala Leu Asn Ala Asp Trp His Ala Asp Cys Phe Arg Cys Cys Asp
         40                  45                  50

TGC AGT GCC TCC CTG TCG CAC CAG TAC TAT GAG AAG GAT GGG CAG CTC         305
Cys Ser Ala Ser Leu Ser His Gln Tyr Tyr Glu Lys Asp Gly Gln Leu
 55                  60                  65                  70

TTC TGC AAG AAG GAC TAC TGG GCC CGC TAT GGC GAG TCC TGC CAT GGG         353
Phe Cys Lys Lys Asp Tyr Trp Ala Arg Tyr Gly Glu Ser Cys His Gly
                 75                  80                  85

TGC TCT GAG CAA ATC ACC AAG GGA CTG GTT ATG GTG GCT GGG GAG CTG         401
Cys Ser Glu Gln Ile Thr Lys Gly Leu Val Met Val Ala Gly Glu Leu
             90                  95                 100

AAG TAC CAC CCC GAG TGT TTC ATC TGC CTC ACG TGT GGG ACC TTT ATC         449
Lys Tyr His Pro Glu Cys Phe Ile Cys Leu Thr Cys Gly Thr Phe Ile
             105                 110                 115

GGT GAC GGG GAC ACC TAC ACG CTG GTG GAG CAC TCC AAG CTG TAC TGC         497
Gly Asp Gly Asp Thr Tyr Thr Leu Val Glu His Ser Lys Leu Tyr Cys
 120                 125                 130

GGG CAC TGC TAC TAC CAG ACT GTG GTG ACC CCC GTC ATC GAG CAG ATC         545
Gly His Cys Tyr Tyr Gln Thr Val Val Thr Pro Val Ile Glu Gln Ile
135                 140                 145                 150

CTG CCT GAC TCC CCT GGC TCC CAC CTG CCC CAC ACC GTC ACC CTG GTG         593
Leu Pro Asp Ser Pro Gly Ser His Leu Pro His Thr Val Thr Leu Val
                155                 160                 165

TCC ATC CCA GCC TCA TCT CAT GGC AAG CGT GGA CTT TCA GTC TCC ATT         641
Ser Ile Pro Ala Ser Ser His Gly Lys Arg Gly Leu Ser Val Ser Ile
                170                 175                 180

GAC CCC CCG CAC GGC CCA CCG GGC TGT GGC ACC GAG CAC TCA CAC ACC         689
Asp Pro Pro His Gly Pro Pro Gly Cys Gly Thr Glu His Ser His Thr
                185                 190                 195

GTC CGC GTC CAG GGA GTG GAT CCG GGC TGC ATG AGC CCA GAT GTG AAG         737
Val Arg Val Gln Gly Val Asp Pro Gly Cys Met Ser Pro Asp Val Lys
    200                 205                 210

AAT TCC ATC CAC GTC GGA GAC CGG ATC TTG GAA ATC AAT GGC ACG CCC         785
Asn Ser Ile His Val Gly Asp Arg Ile Leu Glu Ile Asn Gly Thr Pro
215                 220                 225                 230

ATC CGA AAT GTG CCC CTG GAC GAG ATT GAC CTG CTG ATT CAG GAA ACC         833
Ile Arg Asn Val Pro Leu Asp Glu Ile Asp Leu Leu Ile Gln Glu Thr
                235                 240                 245

AGC CGC CTG CTC CAG CTG ACC CTC GAG CAT GAC CCT CAC GAT ACA CTG         881
Ser Arg Leu Leu Gln Leu Thr Leu Glu His Asp Pro His Asp Thr Leu
                250                 255                 260

GGC CAC GGG CTG GGG CCT GAG ACC AGC CCC CTG AGC TCT CCG GCT TAT         929
Gly His Gly Leu Gly Pro Glu Thr Ser Pro Leu Ser Ser Pro Ala Tyr
                265                 270                 275

ACT CCC AGC GGG GAG GCG GGC AGC TCT GCC CGG CAG AAA CCT GTC TTG         977
Thr Pro Ser Gly Glu Ala Gly Ser Ser Ala Arg Gln Lys Pro Val Leu
```

|  |  |  |  |  |  |  |  |  |  |  |  |  |  |  |  |  |
|---|---|---|---|---|---|---|---|---|---|---|---|---|---|---|---|---|
|  |  |  | 280 |  |  |  | 285 |  |  |  | 290 |  |  |  |  |  |
| AGG | AGC | TGC | AGC | ATC | GAC | AGG | TCT | CCG | GGC | GCT | GGC | TCA | CTG | GGC | TCC | 1025 |
| Arg | Ser | Cys | Ser | Ile | Asp | Arg | Ser | Pro | Gly | Ala | Gly | Ser | Leu | Gly | Ser |  |
| 295 |  |  |  |  | 300 |  |  |  |  | 305 |  |  |  |  | 310 |  |
| CCG | GCC | TCC | CAG | CGC | AAG | GAC | CTG | GGT | CGC | TCT | GAG | TCC | CTC | CGC | GTA | 1073 |
| Pro | Ala | Ser | Gln | Arg | Lys | Asp | Leu | Gly | Arg | Ser | Glu | Ser | Leu | Arg | Val |  |
|  |  |  |  | 315 |  |  |  |  | 320 |  |  |  |  | 325 |  |  |
| GTC | TGC | CGG | CCA | CAC | CGC | ATC | TTC | CGG | CCG | TCG | GAC | CTC | ATC | CAC | GGG | 1121 |
| Val | Cys | Arg | Pro | His | Arg | Ile | Phe | Arg | Pro | Ser | Asp | Leu | Ile | His | Gly |  |
|  |  |  | 330 |  |  |  |  | 335 |  |  |  |  | 340 |  |  |  |
| GAG | GTG | CTG | GGC | AAG | GGC | TGC | TTC | GGC | CAG | GCT | ATC | AAG | GTG | ACA | CAC | 1169 |
| Glu | Val | Leu | Gly | Lys | Gly | Cys | Phe | Gly | Gln | Ala | Ile | Lys | Val | Thr | His |  |
|  |  | 345 |  |  |  |  | 350 |  |  |  |  | 355 |  |  |  |  |
| CGT | GAG | ACA | GGT | GAG | GTG | ATG | GTG | ATG | AAG | GAG | CTG | ATC | CGG | TTC | GAC | 1217 |
| Arg | Glu | Thr | Gly | Glu | Val | Met | Val | Met | Lys | Glu | Leu | Ile | Arg | Phe | Asp |  |
| 360 |  |  |  |  | 365 |  |  |  |  | 370 |  |  |  |  |  |  |
| GAG | GAG | ACC | CAG | AGG | ACG | TTC | CTC | AAG | GAG | GTG | AAG | GTC | ATG | CGA | TGC | 1265 |
| Glu | Glu | Thr | Gln | Arg | Thr | Phe | Leu | Lys | Glu | Val | Lys | Val | Met | Arg | Cys |  |
| 375 |  |  |  |  | 380 |  |  |  |  | 385 |  |  |  |  | 390 |  |
| CTG | GAA | CAC | CCC | AAC | GTG | CTC | AAG | TTC | ATC | GGG | GTG | CTC | TAC | AAG | GAC | 1313 |
| Leu | Glu | His | Pro | Asn | Val | Leu | Lys | Phe | Ile | Gly | Val | Leu | Tyr | Lys | Asp |  |
|  |  |  |  | 395 |  |  |  |  | 400 |  |  |  |  | 405 |  |  |
| AAG | AGG | CTC | AAC | TTC | ATC | ACT | GAG | TAC | ATC | AAG | GGC | GGC | ACG | CTC | CGG | 1361 |
| Lys | Arg | Leu | Asn | Phe | Ile | Thr | Glu | Tyr | Ile | Lys | Gly | Gly | Thr | Leu | Arg |  |
|  |  |  | 410 |  |  |  |  | 415 |  |  |  |  | 420 |  |  |  |
| GGC | ATC | ATC | AAG | AGC | ATG | GAC | AGC | CAG | TAC | CCA | TGG | AGC | CAG | AGA | GTG | 1409 |
| Gly | Ile | Ile | Lys | Ser | Met | Asp | Ser | Gln | Tyr | Pro | Trp | Ser | Gln | Arg | Val |  |
|  |  | 425 |  |  |  |  | 430 |  |  |  |  | 435 |  |  |  |  |
| AGC | TTT | GCC | AAG | GAC | ATC | GCA | TCA | GGG | ATG | GCC | TAC | CTC | CAC | TCC | ATG | 1457 |
| Ser | Phe | Ala | Lys | Asp | Ile | Ala | Ser | Gly | Met | Ala | Tyr | Leu | His | Ser | Met |  |
| 440 |  |  |  |  | 445 |  |  |  |  | 450 |  |  |  |  |  |  |
| AAC | ATC | ATC | CAC | CGA | GAC | CTC | AAC | TCC | CAC | AAC | TGC | CTG | GTC | CGC | GAG | 1505 |
| Asn | Ile | Ile | His | Arg | Asp | Leu | Asn | Ser | His | Asn | Cys | Leu | Val | Arg | Glu |  |
| 455 |  |  |  |  | 460 |  |  |  |  | 465 |  |  |  |  | 470 |  |
| AAC | AAG | AAT | GTG | GTG | GTG | GCT | GAC | TTC | GGG | CTG | GCG | CGT | CTC | ATG | GTG | 1553 |
| Asn | Lys | Asn | Val | Val | Val | Ala | Asp | Phe | Gly | Leu | Ala | Arg | Leu | Met | Val |  |
|  |  |  |  | 475 |  |  |  |  | 480 |  |  |  |  | 485 |  |  |
| GAC | GAG | AAG | ACT | CAG | CCT | GAG | GGC | CTG | CGG | AGC | CTC | AAG | AAG | CCA | GAC | 1601 |
| Asp | Glu | Lys | Thr | Gln | Pro | Glu | Gly | Leu | Arg | Ser | Leu | Lys | Lys | Pro | Asp |  |
|  |  |  | 490 |  |  |  |  | 495 |  |  |  |  | 500 |  |  |  |
| CGC | AAG | AAG | CGC | TAC | ACC | GTG | GTG | GGC | AAC | CCC | TAC | TGG | ATG | GCA | CCT | 1649 |
| Arg | Lys | Lys | Arg | Tyr | Thr | Val | Val | Gly | Asn | Pro | Tyr | Trp | Met | Ala | Pro |  |
|  |  | 505 |  |  |  |  | 510 |  |  |  |  | 515 |  |  |  |  |
| GAG | ATG | ATC | AAC | GGC | CGC | AGC | TAT | GAT | GAG | AAG | GTG | GAT | GTG | TTC | TCC | 1697 |
| Glu | Met | Ile | Asn | Gly | Arg | Ser | Tyr | Asp | Glu | Lys | Val | Asp | Val | Phe | Ser |  |
| 520 |  |  |  |  | 525 |  |  |  |  | 530 |  |  |  |  |  |  |
| TTT | GGG | ATC | GTC | CTG | TGC | GAG | ATC | ATC | GGG | CGG | GTG | AAC | GCA | GAC | CCT | 1745 |
| Phe | Gly | Ile | Val | Leu | Cys | Glu | Ile | Ile | Gly | Arg | Val | Asn | Ala | Asp | Pro |  |
| 535 |  |  |  |  | 540 |  |  |  |  | 545 |  |  |  |  | 550 |  |
| GAC | TAC | CTG | CCC | CGC | ACC | ATG | GAC | TTT | GGC | CTC | AAC | GTG | CGA | GGA | TTC | 1793 |
| Asp | Tyr | Leu | Pro | Arg | Thr | Met | Asp | Phe | Gly | Leu | Asn | Val | Arg | Gly | Phe |  |
|  |  |  |  | 555 |  |  |  |  | 560 |  |  |  |  | 565 |  |  |
| CTG | GAC | CGC | TAC | TGC | CCC | CCA | AAC | TGC | CCC | CCG | AGC | TTC | TTC | CCC | ATC | 1841 |
| Leu | Asp | Arg | Tyr | Cys | Pro | Pro | Asn | Cys | Pro | Pro | Ser | Phe | Phe | Pro | Ile |  |
|  |  |  | 570 |  |  |  |  | 575 |  |  |  |  | 580 |  |  |  |
| ACC | GTG | CGC | TGT | TGC | GAT | CTG | GAC | CCC | GAG | AAG | AGG | CCA | TCC | TTT | GTG | 1889 |
| Thr | Val | Arg | Cys | Cys | Asp | Leu | Asp | Pro | Glu | Lys | Arg | Pro | Ser | Phe | Val |  |
|  |  | 585 |  |  |  |  | 590 |  |  |  |  | 595 |  |  |  |  |
| AAG | CTG | GAA | CAC | TGG | CTG | GAG | ACC | CTC | CGC | ATG | CAC | CTG | GCC | GGC | CAC | 1937 |
| Lys | Leu | Glu | His | Trp | Leu | Glu | Thr | Leu | Arg | Met | His | Leu | Ala | Gly | His |  |

```
                    600                         605                         610
CTG  CCA  CTG  GGC  CCA  CAG  CTG  GAG  CAG  CTG  GAC  AGA  GGT  TTC  TGG  GAG    1985
Leu  Pro  Leu  Gly  Pro  Gln  Leu  Glu  Gln  Leu  Asp  Arg  Gly  Phe  Trp  Glu
615                 620                      625                           630

ACC  TAC  CGG  CGC  GGC  GAG  AGC  GGA  CTG  CCT  GCC  CAC  CCT  GAG  GTC  CCC    2033
Thr  Tyr  Arg  Arg  Gly  Glu  Ser  Gly  Leu  Pro  Ala  His  Pro  Glu  Val  Pro
                    635                      640                           645

GAC  TGAGCCAGGG  CCACTCAGCT  GCCCCTGTCC  CCACCTCTGG  AGAATCCACC                   2086
Asp

CCCACCAGAT  TCCTCCGCGG  GAGGTGGCCC  TCAGCTGGGA  CAGTGGGGAC  CCAGGCTTCT            2146

CCTCAGAGCC  AGGCCCTGAC  TTGCCTTCTC  CCACCCCGTG  GACCGCTTCC  CCTGCCTTCT            2206

CTCTGCCGTG  GCCCAGAGCC  GGCCCAGCTG  CACACACACA  CCATGCTCTC  GCCCTGCTGT            2266

AACCTCTGTC  TTGGCAGGGC  TGTCCCCTCT  TGCTTCTCCT  TGCATGAGCT  GGAGGGCCTG            2326

TGTGAGTTAC  GCCCCTTTCC  ACACGCCGCT  GCCCCAGCAA  CCCTGTTCAC  GCTCCACCTG            2386

TCTGGTCCAT  AGCTCCCTGG  AGGCTGGGCC  AGGAGGCAGC  CTCCGAACCA  TGCCCATAT             2446

AACGCTTGGG  TGCGTGGGAG  GGCGCACATC  AGGGCAGAGG  CCAAGTTCCA  GGTGTCTGTG            2506

TTCCCAGGAA  CCAAATGGGG  AGTCTGGGGC  CCGTTTTCCC  CCCAGGGGGT  GTCTAGGTAG            2566

CAACAGGTAT  CGAGGACTCT  CCAAACCCCC  AAAGCAGAGA  GAGGGCTGAT  CCCATGGGGC            2626

GGAGGTCCCC  AGTGGCTGAG  CAAACAGCCC  CTTCTCTCGC  TTTGGGTCTT  TTTTTTGTTT            2686

CTTTCTTAAA  GCCACTTTAG  TGAGAAGCAG  GTACCAAGCC  TCAGGGTGAA  GGGGGTCCCT            2746

TGAGGGAGCG  TGGAGCTGCG  GTGCCCTGGC  CGGCGATGGG  GAGGAGCCGG  CTCCGGCAGT            2806

GAGAGGATAG  GCACAGTGGA  CCGGGCAGGT  GTCCACCAGC  AGCTCAGCCC  CTGCAGTCAT            2866

CTCAGAGCCC  CTTCCCGGGC  CTCTCCCCCA  AGGCTCCCTG  CCCCTCCTCA  TGCCCCTCTG            2926

TCCTCTGCGT  TTTTTCTGTG  TAATCTATTT  TTTAAGAAGA  GTTTGTATTA  TTTTTTCATA            2986

CGGCTGCAGC  AGCAGCTGCC  AGGGGCTTGG  GATTTTATTT  TTGTGGCGGG  CGGGGGTGGG            3046

AGGGCCATTT  TGTCACTTTG  CCTCAGTTGA  GCATCTAGGA  AGTATTAAAA  CTGTGAAGCT            3106

TTCTCAGTGC  ACTTTGAACC  TGGAAAACAA  TCCAACAGG   CCCGTGGGAC  CATGACTTAG            3166

GGAGGTGGGA  CCCACCCACC  CCCATCCAGG  AACCGTGACG  TCCAAGGAAC  CAAACCCAGA            3226

CGCAGAACAA  TAAAATAAAT  TCCGTACTCC  CCACCC                                       3262
```

( 2 ) INFORMATION FOR SEQ ID NO:42:

( i ) SEQUENCE CHARACTERISTICS:
        ( A ) LENGTH: 647 amino acids
        ( B ) TYPE: amino acid
        ( D ) TOPOLOGY: linear ( i i ) MOLECULE TYPE: protein ( x i ) SEQUENCE DESCRIPTION: SEQ ID NO:42:

```
Met  Arg  Leu  Thr  Leu  Leu  Cys  Cys  Thr  Trp  Arg  Glu  Glu  Arg  Met  Gly
 1              5                        10                          15

Glu  Glu  Gly  Ser  Glu  Leu  Pro  Val  Cys  Ala  Ser  Cys  Gly  Gln  Arg  Ile
               20                        25                      30

Tyr  Asp  Gly  Gln  Tyr  Leu  Gln  Ala  Leu  Asn  Ala  Asp  Trp  His  Ala  Asp
                35                       40                      45

Cys  Phe  Arg  Cys  Cys  Asp  Cys  Ser  Ala  Ser  Leu  Ser  His  Gln  Tyr  Tyr
          50                       55                      60

Glu  Lys  Asp  Gly  Gln  Leu  Phe  Cys  Lys  Lys  Asp  Tyr  Trp  Ala  Arg  Tyr
65                       70                       75                      80
```

```
Gly Glu Ser Cys His Gly Cys Ser Glu Gln Ile Thr Lys Gly Leu Val
             85                  90                      95
Met Val Ala Gly Glu Leu Lys Tyr His Pro Glu Cys Phe Ile Cys Leu
            100                 105                 110
Thr Cys Gly Thr Phe Ile Gly Asp Gly Asp Thr Tyr Leu Val Glu
            115                 120                 125
His Ser Lys Leu Tyr Cys Gly His Cys Tyr Tyr Gln Thr Val Val Thr
130                     135                 140
Pro Val Ile Glu Gln Ile Leu Pro Asp Ser Pro Gly Ser His Leu Pro
145                     150                 155                 160
His Thr Val Thr Leu Val Ser Ile Pro Ala Ser Ser His Gly Lys Arg
                    165                 170                 175
Gly Leu Ser Val Ser Ile Asp Pro Pro His Gly Pro Pro Gly Cys Gly
                180                 185                 190
Thr Glu His Ser His Thr Val Arg Val Gln Gly Val Asp Pro Gly Cys
            195                 200                 205
Met Ser Pro Asp Val Lys Asn Ser Ile His Val Gly Asp Arg Ile Leu
        210                 215                 220
Glu Ile Asn Gly Thr Pro Ile Arg Asn Val Pro Leu Asp Glu Ile Asp
225                     230                 235                 240
Leu Leu Ile Gln Glu Thr Ser Arg Leu Leu Gln Leu Thr Leu Glu His
                    245                 250                 255
Asp Pro His Asp Thr Leu Gly His Gly Leu Gly Pro Glu Thr Ser Pro
            260                 265                 270
Leu Ser Ser Pro Ala Tyr Thr Pro Ser Gly Glu Ala Gly Ser Ser Ala
        275                 280                 285
Arg Gln Lys Pro Val Leu Arg Ser Cys Ser Ile Asp Arg Ser Pro Gly
    290                 295                 300
Ala Gly Ser Leu Gly Ser Pro Ala Ser Gln Arg Lys Asp Leu Gly Arg
305                 310                 315                 320
Ser Glu Ser Leu Arg Val Val Cys Arg Pro His Arg Ile Phe Arg Pro
                325                 330                 335
Ser Asp Leu Ile His Gly Glu Val Leu Gly Lys Gly Cys Phe Gly Gln
            340                 345                 350
Ala Ile Lys Val Thr His Arg Glu Thr Gly Glu Val Met Val Met Lys
        355                 360                 365
Glu Leu Ile Arg Phe Asp Glu Glu Thr Gln Arg Thr Phe Leu Lys Glu
    370                 375                 380
Val Lys Val Met Arg Cys Leu Glu His Pro Asn Val Leu Lys Phe Ile
385                 390                 395                 400
Gly Val Leu Tyr Lys Asp Lys Arg Leu Asn Phe Ile Thr Glu Tyr Ile
                405                 410                 415
Lys Gly Gly Thr Leu Arg Gly Ile Ile Lys Ser Met Asp Ser Gln Tyr
            420                 425                 430
Pro Trp Ser Gln Arg Val Ser Phe Ala Lys Asp Ile Ala Ser Gly Met
        435                 440                 445
Ala Tyr Leu His Ser Met Asn Ile Ile His Arg Asp Leu Asn Ser His
    450                 455                 460
Asn Cys Leu Val Arg Glu Asn Lys Asn Val Val Ala Asp Phe Gly
465                 470                 475                 480
Leu Ala Arg Leu Met Val Asp Glu Lys Thr Gln Pro Glu Gly Leu Arg
                485                 490                 495
Ser Leu Lys Lys Pro Asp Arg Lys Lys Arg Tyr Thr Val Val Gly Asn
            500                 505                 510
```

| | | | | | | | | | | | | | | | |
|---|---|---|---|---|---|---|---|---|---|---|---|---|---|---|---|
| Pro | Tyr | Trp 515 | Met | Ala | Pro | Glu | Met 520 | Ile | Asn | Gly | Arg | Ser 525 | Tyr | Asp | Glu |
| Lys | Val 530 | Asp | Val | Phe | Ser | Phe 535 | Gly | Ile | Val | Leu | Cys 540 | Glu | Ile | Ile | Gly |
| Arg 545 | Val | Asn | Ala | Asp | Pro 550 | Asp | Tyr | Leu | Pro | Arg 555 | Thr | Met | Asp | Phe | Gly 560 |
| Leu | Asn | Val | Arg | Gly 565 | Phe | Leu | Asp | Arg | Tyr 570 | Cys | Pro | Pro | Asn | Cys 575 | Pro |
| Pro | Ser | Phe | Phe 580 | Pro | Ile | Thr | Val | Arg 585 | Cys | Cys | Asp | Leu | Asp 590 | Pro | Glu |
| Lys | Arg | Pro 595 | Ser | Phe | Val | Lys | Leu 600 | Glu | His | Trp | Leu | Glu 605 | Thr | Leu | Arg |
| Met | His 610 | Leu | Ala | Gly | His | Leu 615 | Pro | Leu | Gly | Pro | Gln 620 | Leu | Glu | Gln | Leu |
| Asp 625 | Arg | Gly | Phe | Trp | Glu 630 | Thr | Tyr | Arg | Arg | Gly 635 | Glu | Ser | Gly | Leu | Pro 640 |
| Ala | His | Pro | Glu | Val 645 | Pro | Asp | | | | | | | | | |

DIAGNOSIS OF WILLIAMS SYNDROME AND WILLIAMS SYNDROME COGNITIVE PROFILE BY ANALYSIS OF THE PRESENCE OR ABSENCE OF A LIM-KINASE GENE

CROSS REFERENCE TO RELATED APPLICATIONS

The present invention is a continuation-in-part of application Ser. No. 08/474,020, filed 7 Jun. 1995, which is a continuation of application Ser. No. 08/041,576, filed 5 Apr. 1993, which are both incorporated herein by reference.

This application was made with Government support under Grant No. R01HL4807 from the NHLBI, Grant No. R01HD29957 from the NICHD, and Grant No. M01-RR00064 from the Public Health Service. The United States Government has certain rights in the invention.

BACKGROUND OF THE INVENTION

The publications and other materials used herein to illuminate the background of the invention, and in particular, cases to provide additional details respecting the practice, are incorporated by reference, and for convenience are referenced in the following text by author and are listed alphabetically by author in the appended bibliography.

The ability to visualize an object (or picture) as a set of parts and construct a replica of the object from those parts is known as visuospatial constructive cognition. Neuroanatomical studies in humans and animals suggest that neurons in the posterior parietal cortex are critical for this process (Capruso et al., 1995). This cognitive function is likely mediated by a network of neurons capable of parallel processing. The molecular mechanisms underlying development of these networks, however, are not understood.

Williams syndrome (WS) is a complex developmental disorder that includes a specific cognitive profile (WSCP) characterized by relative strength in language and auditory rote memory and pronounced weakness in visuospatial constructive cognition (Udwin et al., 1987; Morris et al., 1988; Dilts et al., 1990; Bellugi et al., 1994; Mervis and Bertrand, in press; Mervis et al., in press). Additional features of WS include congenital heart and vascular disease, dysmorphic facial features, infantile hypercalcemia, mental retardation, and a characteristic personality. Most individuals with WS have mild or moderate mental retardation (mean IQ ranging from 55–60), but some have borderline normal intelligence or severe mental retardation. The characteristic personality includes excessive friendliness, loquaciousness, oversensitivity to the feelings of others, and extreme anxiety to please. This combination of features results in a remarkable phenotype that is readily distinguished from other disorders involving mental retardation. The incidence of WS is estimated to be 1 in 20,000 live births.

The visuospatial constructive cognitive deficit observed in WS is best demonstrated by tasks involving pattern construction. Performance of these tasks depends on an individual's ability to see an object in terms of a set of parts specified by the researcher and then use those parts to construct a replica of the pictured object. Specifically, individuals are shown a picture of a block design and must construct the corresponding pattern using cubes of varying colors and designs. Individuals with WS typically have difficulty constructing even simple patterns, such as a checkerboard consisting of four cubes. As a result, individuals with WS have marked difficulty in tasks involving the use of a pattern to assemble an object (e.g. building a model or assembling a simple piece of furniture).

Approximately 77% of individuals with WS have clinically apparent supravalvular aortic stenosis (SVAS), an obstructive vascular disease (Lowery et al., 1995). SVAS can be inherited as part of WS or as an isolated, autosomal dominant trait (Curran et al, 1993; Ewart et al., 1993b; Morris et al., 1993; Ewart et al., 1994). SVAS may be associated with some connective tissue abnormalities seen in WS, but other WS features are not observed. In particular, autosomal dominant SVAS is not associated with impaired visuospatial constructive cognition. Recently, genetic linkage and mutational analyses were used to show that mutations in elastin (ELN) cause autosomal dominant SVAS (Ewart et al., 1993a; Curran et al., 1993; Morris et al., 1993; Ewart et al., 1994). Known SVAS-associated mutations in ELN include a translocation, an intragenic deletion, and missense and nonsense mutations (Curran et al., 1993; Olson et al., 1995; unpublished data).

Because there is a phenotypic link between SVAS and WS, it was hypothesized that mutations involving ELN might also contribute to WS. It was discovered that WS results from submicroscopic deletions of chromosome 7q11.23 (Ewart et al., 1993a). Inherited or de novo deletion of one ELN allele was identified in 239 of 240 WS individuals (Ewart et al., 1993a; Lowery et al., 1995; and our unpublished data). These data indicated that ELN mutations cause isolated, autosomal dominant SVAS and that hemizygosity at the ELN locus is responsible for vascular pathology in WS. ELN hemizygosity may also account for some connective tissue abnormalities observed in individuals with autosomal dominant SVAS or WS, including premature aging of skin, some WS facial features, diverticulosis of the bladder and colon, hoarse voice, hernias and joint abnormalities. ELN mutations, however, do not account for all features of WS and are not the cause of impaired visuospatial constructive cognition. Because genomic deletions responsible for WS extend well beyond the ELN locus (unpublished data), it was hypothesized that WS is a contiguous gene deletion syndrome (Ewart et al., 1993a).

Here is reported the identification and characterization of two families with a partial WS phenotype, consisting of SVAS, some WS facial features, and impaired visuospatial constructive cognition, but lacking other features of this disorder. Affected members of these families harbor smaller chromosomal deletions (83.6 and ~300 kb) than those identified in individuals with classic WS (>500 kb), an observation that supports the hypothesis that WS is a contiguous gene deletion syndrome (Ewart et al., 1993a; Gilbert-Dussardier et al., 1995). DNA sequence analyses of the 83.6 kb deletion region have revealed, in addition to ELN, LIM-kinase1 (LIMK1), a gene which encodes a protein kinase with LIM domains (Mizuno et al., 1994; Bernard et al., 1994). No other genes were identified in the region. Northern and in situ hybridization analyses indicate that LIMK1 is strongly expressed in discrete regions of the brain. Because ELN mutations cause vascular disease but not cognitive abnormalities, these data indicate that LIMK1 hemizygosity contributes to impaired visuospatial constructive cognition in WS.

SUMMARY OF THE INVENTION

To identify genes important for human cognitive development, Williams syndrome (WS), a developmental disorder that includes poor visuospatial constructive cognition, has been studied. Two families are here described with a partial WS phenotype; affected members have the specific WS cognitive profile and vascular disease, but lack other WS features. Submicroscopic chromosome 7q11.23 deletions cosegregate with this phenotype in both families. DNA sequence analyses of the region affected by the smallest (83.6 kb) deletion revealed two genes, elastin (ELN) and LIM-kinase1 (LIMK1). The latter encodes a novel protein kinase with LIM domains and is strongly expressed in the brain. Because ELN mutations cause vascular disease but not cognitive abnormalities, these data implicate LIMK1 hemizygosity in impaired visuospatial constructive cognition.

BRIEF DESCRIPTION OF THE FIGURES

FIGS. 3A and 3B. Predicted structure of LIMK1. A) DNA sequence analyses were used to predict the amino acid sequence of LIMK1. Two possible start sites are indicated by asterisks. The second start site shows slightly better conformity to the Kozak consensus sequence (Kozak, 1989). Individual amino acids involved in zinc-finger formation as part of two LIM domains are indicated by lightly shaded boxes. A DHR domain between residues 165 and 258 is denoted by a darkly shaded box. A possible PEST domain identified in residues 264– 289 is indicated by a lightly shaded box. A basic domain located in residues 499–506 (empty box) may mediate nuclear localization. The kinase domain, indicated by horizontal black bars, is divided into eleven subdomains (I–XI). Conserved amino acids in the kinase domain are indicated by empty boxes (Hanks et al., 1988). B) Schematic representation of LIMK1 indicating major domains.

FIG. 5A shows the results of Northern analyses. Human adult, fetal, and brain Northern blots (poly[A]$^+$RNA, 2 μg per lane) were hybridized with LIMK1, ELN, and β-actin probes. LIMK1 hybridized with an ~3.3 kb mRNA in most tissues examined, with highest expression in both fetal and adult brain. ELN also hybridized with an ~3.3 kb mRNA with highest expression in heart, pancreas, and fetal lung. FIG. 5B shows a graphic representation of LIMK1 expression levels after normalization to β-actin.

DETAILED DESCRIPTION OF THE INVENTION

Figure 1A:
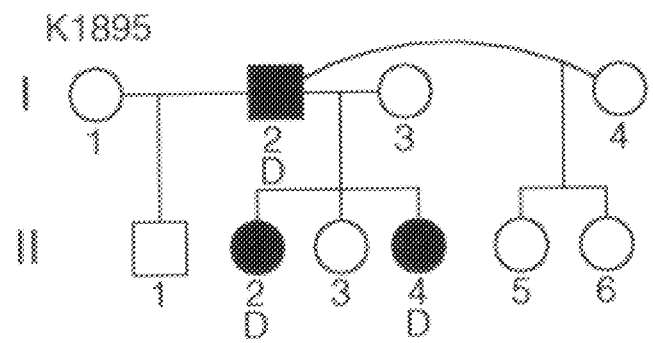
FIGS. 1A and 1B. Co-inheritance of a partial WS phenotype and deletions involving ELN and LIMK1 in kindreds 1895 and 2049. A) Pedigree structure and phenotypic assignments for K1895 are shown. Individuals with SVAS are indicated by filled, upper half-circles (females) or squares (males). Individuals with the WSCP are indicated by filled, lower half-circles or squares. Phenotypically unaffected individuals are indicated by empty circles or squares. Individuals I-2, II-2, and II-4 were phenotypically affected with both SVAS and the WSCP. No features of WS were identified in other members of this kindred. Individuals harboring an ~300 kb deletion of chromosome 7q11.23, including the entire ELN and LIMK1 genes, are indicated by a D. Note that this deletion cosegregates with the SVAS/WSCP phenotype in this family. B) Phenotypic designations for members of K2049 are as described for FIG. 1A, except that an uncertain phenotype is indicated by stippling. Oligonucleotide primers 403f (5'-CCTACCTTTCCTGCTGCAAT-3' SEQ ID NO:37) and 403r (5'-AAAAAGAGGCCGGGTATGGT-3' SEQ ID NO:38) were used to define a novel 403-bp PCR product that spans the 83.6-kb deletion in affected members of this family. The results of PCR analyses are shown below in the lane corresponding to each symbol. Note that this 83.6-kb deletion cosegregates with SVAS/WSCP in this family but that penetrance is incomplete.

Williams syndrome is a contiguous gene disorder resulting from mutations in or deletion of at least three distinct genes. These genes are located on chromosome 7 in the 7q11.23 region. Two of the genes involved in Williams syndrome are elastin (ELN) and LIM-Kinase1 (LIMK1). A mimimum of at least one more gene located greater than 300 kb 3' of LIMK1 is also involved in Williams syndrome. The identity of this gene or genes has not yet been established. Williams syndrome results from loss of all of the involved genes. Loss of only one or two of the involved genes causes other disorders which involve only some of the aspects of Williams syndrome. A partial loss of functional elastin due to the presence of only one wild-type elastin gene results in the condition known as supravalvular aortic stenosis (SVAS) which is an obstructive vascular disease. Elastin is a structural protein important in large arteries, lungs and skin. A partial loss of both functional elastin and LIMK1 due to the presence of only one wild-type copy of each of the corresponding genes results in the condition known as Williams syndrome cognitive profile (WSCP). LIMK1 is a protein kinase which is highly expressed in the brain and is important in visuospatial constructive cognition. A functional loss of not only elastin and LIMK1 but also at least one more protein encoded by a gene 3' of LIMK1 results in development of classic Williams syndrome. Persons with SVAS and WSCP have only a subset of the characteristics seen in persons with classic Williams syndrome. Persons with Williams syndrome have been found to have a deletion of greater than 500 kb in the 7q11.23 region of one chromosome, this deletion including at least a portion of ELN, LIMK1 and at least 300 kb 3' of LIMK1. Although some families have been found which show deletions of ELN and LIMK1 but which deletions do not extend far enough 3' to delete a third gene (these families thus being characterized as having WSCP), in 99% of the cases studied a person who has a deletion in ELN is found to have a deletion of greater than 500 kb such that the deletion includes not only ELN but also LIMKI and at least one other gene 3' of LIMK1 thus resulting in classic Williams syndrome. This is significant in that a hemizygous deletion of ELN indicates a 99% chance that the patient has classic Williams syndrome and not simply SVAS or WSCP.

It is here concluded that LIMK1 hemizygosity contributes to impaired visuospatial constructive cognition in WS. This conclusion is supported by the following observations: 1) SVAS and the WSCP are co-inherited in K1895 and K2049, as well as in classic WS, suggesting that the genes responsible for these two phenotypes are closely linked; 2) ELN and LIMK1 are contiguous genes that are both disrupted by an 83.6-kb deletion that cosegregates with SVAS and the WSCP in K2049; 3) DNA sequence analyses of the 83.6-kb deletion region and 24 kb of flanking sequence revealed only ELN and LIMK1; no other genes were identified in these sequences; 4) LIMK1 is highly expressed in the brain, consistent with its possible function in cognitive development; and 5) intragenic deletions and point mutations affecting only ELN cause SVAS but no cognitive impairment, indicating that ELN hemizygosity is not sufficient to cause impaired visuospatial constructive cognition in WS.

It is also very unlikely that ELN mutations are necessary for impaired visuospatial constructive cognition in WS. First, no correlation exists between the severity of the vascular disease and the severity of cognitive impairment in WS. Second, ELN is a structural protein that is important for the development of elastic fibers in large arteries, lungs, and skin, but these elastic fibers are not found in the brain. Finally, ELN is not expressed in neurons and glial cells of the brain (R. Mecham, personal communication). Therefore, it is concluded that ELN mutations and secondary vascular disease are not sufficient, and almost certainly not necessary, for impaired visuospatial constructive cognition in WS.

The argument that LIMK1 hemizygosity contributes to impaired cognition would be confirmed by the identification of individuals with intragenic mutations of this gene. Preliminary experiments aimed at ascertainment of such individuals have not been successful. This is not surprising, because these individuals are probably rare and likely have a very subtle phenotype. To exclude the involvement of additional genes in development of the WSCP, the 83.6-kb deletion region and 24 kb of flanking sequence were sequenced. Programs designed to identify coding regions revealed only two genes, LIMK1 and ELN. While these analyses did not absolutely exclude the presence of a third gene, the sensitivity of the search algorithms was demonstrated by their identification of 15 of the 16 LIMK1 exons. It is highly likely, therefore, that all genes in this region were detected.

Previous studies of LIMK1 expression are consistent with a role for this gene in cognitive development. Northern analyses in rat showed LIMK1 expression in multiple tissues, with mRNA levels being highest in the brain (Mizuno et al., 1994). Bernard et al. (1994) identified ubiquitous murine embryonal expression, but found significant mRNA levels only in the adult brain. In situ hybridization and immunohistochemical studies performed in mice and humans localized LIMK1 mRNA and protein exclusively to neurons (basal ganglia, Purkinje cells, and pyramidal neurons; Bernard et al., 1994). Using Northern blot analysis, Proschel et al. (1995) demonstrated expression of LIMK1 in adult murine spinal cord, cortex, cerebellum, and placenta, with lower levels of mRNA in several other tissues. In situ hybridization of tissues collected during various stages of murine development indicated expression of LIMK1 in the developing brain, including the subpial layers of the frontal cortex, the midbrain roof, tectum, cerebellum, and neural epithelium of the olfactory bulb. In the adult mouse, LIMK1 expression persisted in the cerebral cortex. Our Northern data indicate expression of LIMK1 in multiple human fetal and adult tissues but mRNA levels were highest in brain. In situ hybridization data presented here also indicate that in developing human tissues, LIMK1 mRNA is predominantly found in brain, a localization consistent with the pattern of LIMK1 expression in the mouse and rat (Bernard et al., 1994; Cheng and Robertson, 1995; Nunoue et al., 1995; Pröschel et al., 1995). The discrete organization of LIMK1 expression in the developing and adult nervous system, with consistent expression in the ependymal layer from which neurons are generated, is consistent with the hypothesis that this gene plays an important role in neural development.

The data suggest that impaired visuospatial constructive cognition in WS results from a quantitative reduction in LIMK1 mRNA and protein. This hypothesis is consistent with recent data examining the role of protein kinases in murine development. Impaired long-term potentiation, spatial learning, and hippocampal development were identified in mice deficient in the brain-specific protein kinases fyn (Grant et al., 1992) and the γ isoform of protein kinase C (Abeliovich et al., 1993a; Abeliovich et al., 1993b). Although the spatial learning deficits observed in these mice were not directly analogous to impaired visuospatial constructive cognition in humans with WS, the data do indicate a role for kinases in neuronal development.

The function of LIMK1 is not known, but the presence of specific functional domains suggests possibilities. LIM domains are zinc-binding motifs first identified in the developmentally important genes lin-11, Isl-1, and mec-3 (Freyd et al., 1990; Karlsson et al., 1990; Way and Chalfie, 1988). LIM domains have been identified in isolation, or in combination with homeodomains, and are thought to modulate cell fate and differentiation (Schmeichel and Beckerle, 1994). LIMK1, by contrast, is unique because it contains a kinase domain in addition to two LIM domains. Predicted amino acid sequence analyses also indicate the presence of a possible PEST domain, a type of sequence that is often found in proteins with short half-lives. This observation suggests that levels of LIMK1 may be tightly regulated. Finally, the predicted amino acid sequence of LIMK1 indicates that cytoskeleton and nuclear localization signals may be present. Biochemical and developmental studies of LIMK1 function will be instrumental in defining the role of this protein in human cognitive development.

The phenotypic variability observed in this study results from variable expression and incomplete penetrance, consistent with results of previous studies of autosomal dominant SVAS and WS (Morris et al., 1988; Ewart et al., 1993a). Variable expression of dysmorphic facial features in individuals with isolated SVAS and classic WS have led to diagnostic confusion in the past (Grimm and Wesselhoeft, 1980), but in this and previous studies, it has been shown that individuals with autosomal dominant SVAS have 6 or fewer of the 16 facial features associated with classic WS. These data indicate that ELN mutations account for SVAS and some WS facial features, but that hemizygosity of another, contiguous gene accounts for other WS facial features. Continued deletional analyses should help define genes that contribute to the full WS phenotype, including those involved in the facial features, mental retardation, and the WS personality.

The DNA sequence analyses for the present studies revealed a high density of Alu repeats within the region deleted in K2049 (6-fold higher than the estimated mean density throughout the human genome; Hwu et al., 1986; Slightom et al., 1994), a density comparable to that found in the genomic region associated with DiGeorge syndrome (Budarf et al., 1995). Both WS and DiGeorge syndrome result from chromosomal rearrangements, which might be driven by the highly repetitive nature of the DNA. In this regard, it is interesting to note that we identified Alu sequences at both breakpoints in K2049, suggesting that a recombinational event between these elements may have been responsible for this deletion. Alu repeats have previously been implicated in an SVAS-associated translocation and in an intragenic deletion of ELN (Curran et al., 1993; Olson et al., 1995).

In summary, it has been here discovered that hemizygosity of LIM-kinase1, a protein kinase gene expressed in the brain, likely leads to impaired visuospatial constructive cognition in Williams syndrome. Further elucidation of the physiologic significance of this gene may result from gene targeting experiments in mice. Analyses of LIMK1 function should provide further insight into human cognitive development.

EXAMPLE 1
Identification of individuals with a partial WS phenotype

If WS is a contiguous gene deletion disorder, individuals with a partial WS phenotype should exist. To test this hypothesis, individuals with SVAS were phenotypically characterized for the presence of additional WS features, including facial appearance, the WSCP, the WS personality, and mental retardation. Phenotypic studies included personal interview, physical examination, two-dimensional and Doppler echocardiography, IQ determination, WS personality assessment, and WSCP analyses.

Clinical characterization of participants

Medical records were reviewed and participants were examined by a clinical geneticist. Craniofacial features scored included dolichocephaly, broad brow, periorbital fullness, stellate iris, bitemporal narrowing, low nasal root, flat mala, full cheeks, long philtrum, small jaw, malocclusion, full nasal tip, wide mouth, full lips, prominent ear lobes, and facial asymmetry. Individuals with classic WS had 9 or more of the 16 features and met the diagnostic criteria of Preus (1984). Affected members of K1895 and K2049 had 0–6 of the 16 facial features and none of these individuals fit the diagnostic criteria for WS. The presence and extent of SVAS was determined by two-dimensional echocardiography and Doppler blood-flow analyses as described by Ensing et al. (1989). Individuals were scored as affected if there was narrowing of the ascending aorta demonstrated on echocardiography or if Doppler peak flow velocities were above normal (normal values for adults: aortic 1.0–1.7 m/s, pulmonary 0.6–0.9 m/s; children: aortic 1.2–1.8 m/s, pulmonary 0.7–1.1 m/s). Velocities within 0.2 m/s greater than the normal range were considered weakly positive. Individuals were also scored as positive if SVAS was documented by medical records of cardiac catheterization or surgery.

Determination of Williams Syndrome Cognitive Profile

The general pattern of cognitive strengths and weaknesses observed in WS (WSCP) has been described in several laboratories (Udwin et al., 1987; Bellugi et al., 1994; Mervis and Bertrand, in press; Mervis et al., in press), but until now, no formal method for assessment has been available. The profile assessment that was proposed is based on performance on the DAS (Elliot, 1990), a standardized measure of cognitive abilities. The DAS was specifically designed to identify relative strengths and weaknesses in cognitive abilities. The six core subtests assess language, spatial (visuospatial constructive cognition), and reasoning abilities. A diagnostic subtest measures auditory rote memory. Thus, the DAS covers all of the skills included in the cognitive profile associated with WS.

Individuals who met one or more of the following criteria were excluded from having the WSCP:

i. pattern construction standard score≧mean of the core subtest scores (visuospatial constructive ability too high relative to overall level of cognitive abilities)

ii. pattern construction standard score≧digit recall standard score (visuospatial constructive ability too high relative to auditory rote memory ability)

iii. pattern construction standard score≧20th percentile (absolute level of visuospatial constructive ability too high)

iv. none of the seven subtest standard scores>1st percentile (absolute level of ability too low).

Individuals who were not excluded were considered to have the WSCP and were evaluated further to determine the strength of their match to the WSCP. A maximum of 4 points could be earned (4 points=excellent fit, 3 points=very good fit, 2 points=good fit, and 0–1 point=poor fit to the WSCP).

i. digit recall standard score>mean of the core subtest standard scores (2 points).

ii. verbal standard scores>pattern construction standard score
   a. definition standard score (naming vocabulary was used for younger children)>pattern construction standard score (1 point).
   b. similarities standard score>pattern construction standard score (1 point).

The DAS was used for individuals who were at least 2 ½ years old. For younger children, the WSCP was assessed using the mental scale of the Bayley Scales of Infant Development (Bayley, 1969; Bayley, 1993). The child was considered to have the WSCP if he or she passed a greater proportion of language items attempted than non-language items. Use of the Bayley to determine if a child's cognitive profile is consistent with the WSCP has been validated in a study comparing very young children with WS to very young children with Down syndrome (Mervis & Bertrand, in press). In the present study, the Bayley measure was used for one child (K1895 II-4), who was 15 months old at the time of assessment.

Individuals who did not complete the DAS were phenotypically characterized with the Wechsler Adult Intelligence Scale-Revised (WAIS-R) whenever possible. Exclusion criteria for the WAIS-R are listed below:
   i. block design standard score>digit span standard score
   ii. block design standard score>20th percentile
   iii. none of the subtest standard scores>1st percentile Individuals who were not excluded on the basis of these criteria were considered to have a cognitive profile consistent with the WSCP if both their digit recall and similarities standard scores were greater than their block-design standard score. Those individuals who could not complete the entire WAIS-R were given the verbal portion of the WAIS-R and the Developmental Test of Visual-Motor Integration (VMI; Beery, 1989). Individuals were excluded from further consideration for the WSCP if their VMI age equivalent was greater than 10 years. Individuals who were not excluded were considered to have a cognitive profile consistent with the WSCP if their standard score on the verbal portion of the WAIS-R was greater than their standard score on the VMI.

Determination of the Williams Syndrome Personality

Each member of K1895 and K2049 and 9 of the 11 individuals with isolated SVAS were independently assessed for the WS personality by two or three examiners (inter-rater agreement=100%). Of the 85 individuals with classic WS, 65 were assessed by two examiners (inter-rater agreement= 98%) and the remainder by one examiner. Twenty-two of the 65 individuals in the control group were assessed by two examiners (inter-rater agreement=95%) and the remainder by one examiner. The following seven WS personality characteristics were evaluated: 1) the presence of an appealing personality; 2) excessive friendliness; 3) loquaciousness; 4) extreme sensitivity to others' feelings; 5) excessive anxiousness to please; 6) very high anxiety; and 7) an extreme interest in people. Phenotypic status was based on the number of characteristics that each individual possessed. Individuals with 4 to 7 of the characteristics were classified as having the WS personality; those with 3 were classified as uncertain; and those with 0 to 2 were classified as not having the WS personality.

Determination of Mental Retardation/Developmental Delay

Intelligence was assessed using the Bayley for children<2 ½ years old, the DAS was used for individuals between the ages of 2 ½ and 18 years, and the WAIS-R was used for individuals who were 18 years or older. All measures were administered according to standard procedures. Individuals who were at least 6 years old were considered to have mental retardation if their standard score was <70 (>2 standard deviations below the standardization sample mean). Individuals who were less than 6 years old were considered to have developmental delay if their standard score was <70.

Results

Phenotypic assignment with respect to WSCP was based, whenever possible, on the pattern of performance on subscales of the Differential Ability Scale (DAS; Elliott, 1990), a standardized measure of cognitive abilities. When the DAS could not be administered, phenotypic assignment was based on performance on subscales of the Wechsler Adult Intelligence Scale-Revised (WAIS-R; Wechsler, 1981), the Developmental Test of Visual Motor Integration (VMI; Beery, 1989) or the Mental Scale of the Bayley Scales of Infant Development (Bayley, 1969; Bayley, 1993). Use of the Bayley to determine if a child's cognitive profile is consistent with the WSCP has been validated in a study comparing very young children with WS to very young children with Down syndrome (Mervis and Bertrand, in press). In the present study, the Bayley measure was used for only one child (K1895 II-4), who was 15 monts old at the time of assessment. Quantitative data resulting from these tests were used to test for the presence of the WSCP, which involves weakness on the pattern construction subtest and strength on the digit recall subtest relative to performance on other subtests. The results of these studies are summarized in Tables 1–3.

To determine the sensitivity of the WSCP assessment, the DAS was also administered to 48 individuals with WS ranging in age from 4 to 47 years (IQ range 35–84). Of these individuals, 45 fit the WSCP; 40 had an excellent fit, 3 had a very good fit, and 2 had a good fit. To determine specificity, the performance of 25 control individuals with below-average IQ (IQ range 30–95) was also examined. Some of these controls had other syndromes (e.g., Down syndrome or Fragile X syndrome); the others had no specific diagnosis. Of these individuals, 23 of 25 definitely did not fit the WSCP. Thus, the WSCP measure has excellent sensitivity (0.94) and specificity (0.92).

The WS personality was assessed by examining individuals for seven personality characteristics commonly found in WS. Standardized assessments of personality could not be used because these methods do not address the unique characteristics included in the WS personality. Individuals who showed at least 4 of 7 of the characteristics were considered to have the WS personality. Individuals who showed 3 characteristics were classified as uncertain. Individuals who showed 2 or fewer characteristics were considered not to have the WS personality. To determine the sensitivity and specificity of our measure, we evaluated 85 individuals with WS and a control group of 65 individuals with mental retardation or borderline normal intelligence. Eighty-three of 85 WS individuals had the WS personality.

TABLE 1

Phenotypic evaluation of individuals with partial WS phenotype and control subjects

| Individual | SVAS | Facies | WSCP | WSP | MR/DD | DEL |
|---|---|---|---|---|---|---|
| K1895 | | | | | | |
| I-2 | + | 3 | + | − | − | D(~300 kb) |
| I-3 | − | 0 | − | − | − | N |
| II-1 | − | 0 | − | − | − | N |
| II-2 | + | 5 | + | − | − | D(~300 kb) |
| II-3 | − | 0 | − | − | − | N |

TABLE 1-continued

Phenotypic evaluation of individuals with partial WS phenotype and control subjects

| Individual | SVAS | Facies | WSCP | WSP | MR/DD | DEL |
|---|---|---|---|---|---|---|
| II-4 | + | 2 | + | − | − | D(~300 kb) |
| II-5 | − | 0 | − | − | − | N |
| II-6 | − | 0 | − | − | − | N |
| K2049 | | | | | | |
| I-1 | + | 4 | + | − | − | D(83.6 kb) |
| II-2 | + | 2 | + | − | − | D(83.6 kb) |
| II-3 | − | 2 | + | − | − | D(83.6 kb) |
| II-4 | + | 0 | + | − | − | D(83.6 kb) |
| II-5 | − | 0 | − | − | − | N |
| II-6 | + | 4 | + | − | − | D(83.6 kb) |
| II-7 | − | 0 | − | − | − | N |
| III-1 | − | 0 | − | − | − | N |
| III-2 | − | 0 | + | − | − | D(83.6 kb) |
| III-3 | + | 0 | U | − | − | D(83.6 kb) |
| III-4 | − | 0 | − | − | − | N |
| III-5 | − | 0 | − | − | − | N |
| III-6 | + | 0 | + | − | + | D(83.6 kb) |
| III-7 | + | 0 | − | − | − | D(83.6 kb) |
| III-8 | − | 0 | − | − | − | N |
| IV-1 | − | 0 | − | − | − | N |
| IV-2 | + | 6 | + | − | − | D(83.6 kb) |
| Classic WS | | | | | | |
| 13759 | + | 13 | + | 6 | + | D(>500 kb) |
| 13946 | + | 16 | + | + | + | D(>500 kb) |
| 14033 | + | 15 | + | + | + | D(>500 kb) |
| 14101 | + | 13 | + | + | + | D(>500 kb) |
| 14576 | − | 14 | + | + | + | D(>500 kb) |
| 15083 | + | 13 | + | + | + | D(>500 kb) |
| 15266 | + | 13 | + | + | + | D(>500 kb) |
| 17402 | + | 13 | + | + | + | D(>500 kb) |
| 18031 | − | 14 | + | + | + | D(>500 kb) |
| 18296 | + | 14 | + | + | + | D(>500 kb) |
| Autosomal Dominant SVAS | | | | | | |
| 12903 | + | 1 | − | 0 | − | N |
| 12905 | + | 3 | − | 0 | − | N |
| 12906 | + | 2 | − | 0 | − | N |
| 12907 | + | 0 | − | 0 | − | N |
| 13222 | + | 1 | − | − | − | N |
| 13835 | + | 0 | − | − | − | N |
| 14104 | + | 1 | − | 0 | − | N |
| 14107 | + | 0 | − | 0 | − | N |
| 17607 | + | 2 | − | 0 | − | N |
| 20583 | + | 2 | − | − | − | N |

Table 1. Phenotypic evaluation was completed in members of two families with a partial WS phenotype (K1895 and K2049), individuals with classic WS, and individuals with autosomal dominant SVAS resulting from ELN mutations. Phenotypic assignments included the presence (+) or absence (−) of SVAS, specific WS cognitive profile (WSCP), and mental retardation or developmental delay (MR/DD). Individuals were assigned 0–7 of 7 possible WS personality characteristics (WSP); individuals were considered affected if they had $\geq 4$ characteristics and unaffected if they had $\leq 2$ characteristics. The number of WS facial features present (Facies) is also indicated (0–16 of 16 possible WS facial features). The phenotypic assessments for WSCP were based on numerical scores obtained from one of the following standardized tests: 1) Differential Ability Scales; 2) Wechsler Adult Intelligence Scale-Revised; or 3) Mental Scale of the Bayley Scales of Infant Development. Individual III-3 of K2049 was characterized as phenotypically uncertain (U) with respect to WSCP because of a seizure disorder treated with anti-convulsant medication. Individual III-6 had mild developmental delay, with an IQ=64; the 95% confidence interval was 58–71 (an IQ score of $\geq 70$ would be in the normal range). The presence (D) or absence (N) of a chromosome 7q11.23 deletion is indicated at right. Note that SVAS, mild WS facial features, and the WSCP cosegregated with deletions in K1895 and K2049. Incomplete penetrance and variable expression were apparent in these kindreds.

TABLE 2

Assessment of WSCP for individuals completing the DAS

| | Exclusion | | | Strength of Fit to WSCP | | |
|---|---|---|---|---|---|---|
| Individual | PC $\geq$ T | PC $\geq$ D | PC $\geq$ 20% | D > T | V > PC | TOTAL |
| K1895 | | | | | | |
| I-2 | | | | 2 | 2 | 4 |
| I-3 | | x | | | | |
| II-1 | x | x | | | | |
| II-2 | | | | 2 | 2 | 4 |
| II-3 | x | | x | | | |
| II-5 | x | | x | | | |
| II-6 | x | x | x | | | |
| K2049 | | | | | | |
| III-1 | x | | x | | | |
| III-2 | | | | 2 | 2 | 4 |
| III-4 | x | | | | | |
| III-5 | | x | | | | |
| III-6 | | | | 2 | 2 | 4 |
| III-7 | | x | | | | |
| III-8 | x | x | | | | |
| IV-1 | | | x | | | |
| IV-2 | | | | 2 | 2 | 4 |
| Classic WS | | | | | | |
| 13759 | | | | 2 | 2 | 4 |
| 13946 | | | | 2 | 2 | 4 |
| 14033 | | | | 2 | 2 | 4 |
| 14101 | | | | 2 | 2 | 4 |
| 14576 | | | | 2 | 2 | 4 |
| 15083 | | | | 2 | 2 | 4 |
| 15266 | | | | 2 | 2 | 4 |
| 17402 | | | | 2 | 2 | 4 |
| 18031 | | | | 2 | 2 | 4 |
| 18296 | | | | 2 | 2 | 4 |
| Autosomal Dominant SVAS | | | | | | |
| 12903 | x | x | x | | | |
| 12905 | x | x | x | | | |
| 12906 | | | x | | | |
| 12907 | x | | x | | | |
| 13222 | x | x | x | | | |
| 13835 | x | x | x | | | |
| 14104 | x | x | x | | | |
| 14107 | x | x | x | | | |
| 17607 | x | x | x | | | |
| 20583 | x | x | x | | | |
| Normal | | | | | | |
| 29998 | x | | x | | | |
| 29999 | | x | x | | | |

Table 2. WSCP evaluation using the DAS was completed in members of K1895, K2049, autosomal dominant SVAS, normal controls, and individuals with classic WS. DAS evaluation included assessment of pattern construction (PC), digit recall (D), verbal abilities (V), and mean standard score for the core subtests (T). The WSCP was excluded if PC$\geq$T, PC$\geq$D, or PC$\geq$20th percentile. For individuals who were not excluded, level of fit to the WSCP was based on total score: 0–1 point=poor fit; 2=good fit; 3=very good fit; 4=excellent fit.

TABLE 3

Assessment of WSCP for individuals who did not complete the DAS

INDIVIDUALS WHO COMPLETED THE WAIS-R

| Individual | Exclusion | | Inclusion | | WSCP |
|---|---|---|---|---|---|
|  | PC ≧ D | PC ≧ 20% | D > PC | V > PC |  |
| K2049 |  |  |  |  |  |
| I-1 |  |  | ◇ | + | + |
| II-2 |  |  | + | + | + |
| II-3 |  |  | + | + | + |
| II-4 |  |  | + | + | + |
| II-5 | + |  |  |  | − |

INDIVIDUALS WHO COMPLETED THE VERBAL WAIS-R AND THE VMI

| Individual | Exclusion VMI AE > 10 years | Inclusion Verbal WAIS-R > VMI | WSCP |
|---|---|---|---|
| K2049 |  |  |  |
| II-6 |  | + | + |
| II-7 | + |  | − |

INDIVIDUAL WHO COMPLETED THE BAYLEY

| Individual | Bayley I % LI > % NLI | Bayley II % LI > % NLI | WSCP |
|---|---|---|---|
| K1895 |  |  |  |
| II-4 | + | + | + |

◇ Digit recall assessment was inappropriate, due to dementia

Table 3. Adults who could not complete the DAS were phenotypically characterized with the Wechsler Adult Intelligence Scale-Revised (WAIS-R) whenever possible. Phenotypic characterizations based on the WAIS-R included assessments of pattern construction (PC; block design subtest), digit recall (D), and verbal abilities (V). Inclusion criteria for Bayley I and Bayley II were based on passing a greater proportion of language items attempted (%LI) than non-language items attempted (%NLI). Individuals II-6 and II-7 of K2049 only completed the verbal portion of the WAIS-R, so additional characterization was completed using the Developmental Test of Visual Motor Integration (VMI). VMI AE=age equivalent for the VMI. Individual II-4 of K1895 was too young to complete the DAS, so phenotypic characterization was carried out using the Bayley test.

Sixty-four out of 65 control individuals did not have the WS personality. Thus, the WS personality measure had a sensitivity of 0.98 and a specificity of 0.98.

Phenotypic characterization of individuals with isolated, autosomal dominant SVAS indicated that these individuals did not manifest the other major features of WS (Table 1 and data not shown). Occasionally, an individual with autosomal dominant SVAS presented with a few WS facial features (≦6 of 16) and/or a hernia, but no other WS phenotypic characteristics were observed. In particular, no one with autosomal dominant SVAS showed evidence of the WSCP. Because these individuals each harbors a mutation (translocation or point mutation) that disrupts one ELN allele, the data indicate that ELN mutations cause vascular disease but not impaired visuospatial constructive cognition.

Figure 1B:
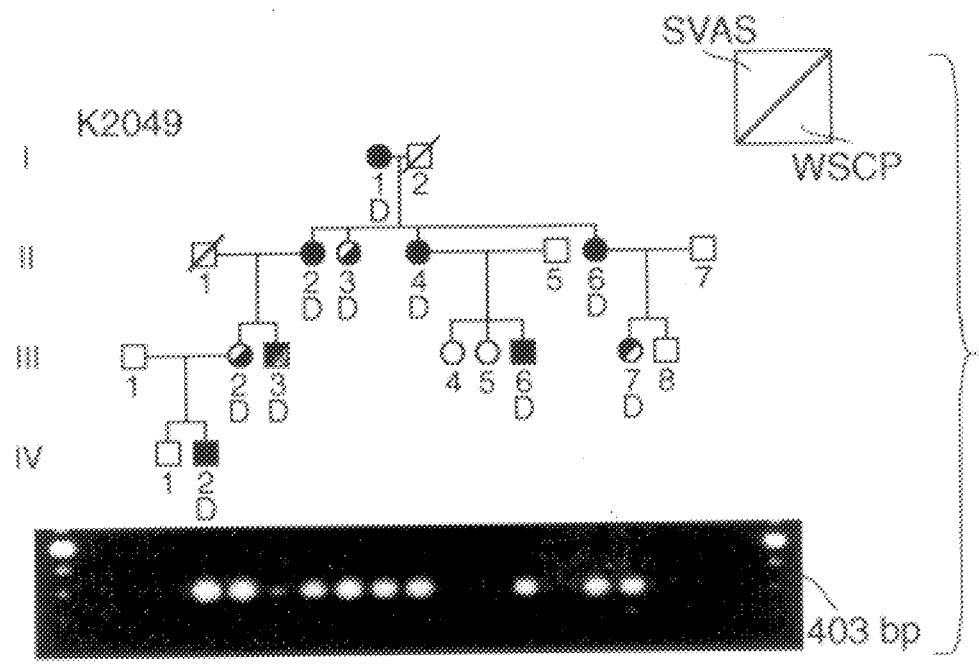

Continued ascertainment and phenotypic characterization revealed two families with a partial WS phenotype (FIGS. 1A and 1B). Most affected members of these families had SVAS, some WS facial features, and the WSCP. These individuals showed levels of verbal ability and auditory short-term memory similar to those of unaffected family members, but their visuospatial constructive abilities were markedly impaired. Affected members lacked other features of WS, including the WS personality and mental retardation (Table 1). Serum calcium levels during infancy were available for only four individuals, but none showed evidence of hypercalcemia (data not shown). No WS phenotypic characteristics were present in unaffected family members.

Previous studies indicate marked intra- and inter-familial variability of expression and incomplete penetrance for autosomal dominant SVAS (Curran et al, 1993; Ewart et al., 1993b; Morris et al., 1993; Ewart et al., 1994). Similar variability was found in individuals with partial WS phenotypes. For example, SVAS was severe and required surgery in two members of K2049 (individuals III-3 and III-7) and had led to early death in three members of K1895 (individuals not shown on pedigree). Other affected members of these kindreds exhibited mild to moderate SVAS, and vascular disease was not clinically apparent in two members of K2049 (individuals II-3 and III-2). Some WS facial features (2–6 of the 16 possible facial characteristics associated with classic WS) were observed in all affected members of K1895 and in 5 of 10 affected members of K2049, but these features did not fulfill the diagnostic criteria for WS (≧9 of 16 facial features). WSCP was observed in all affected members of K1895 and in 8 of 10 affected members of K2049; one member of K2049 did not fulfill the diagnostic criteria for WSCP (individual III-7) and one individual (III-3) was classified as uncertain. These phenotypic studies indicate autosomal dominant co-inheritance of SVAS, some WS facial features, and WSCP in two families with variable phenotypic expression and incomplete penetrance. Identification of individuals with a partial WS phenotype supports the hypothesis that WS is a contiguous gene deletion syndrome.

EXAMPLE 2

Figure 2:
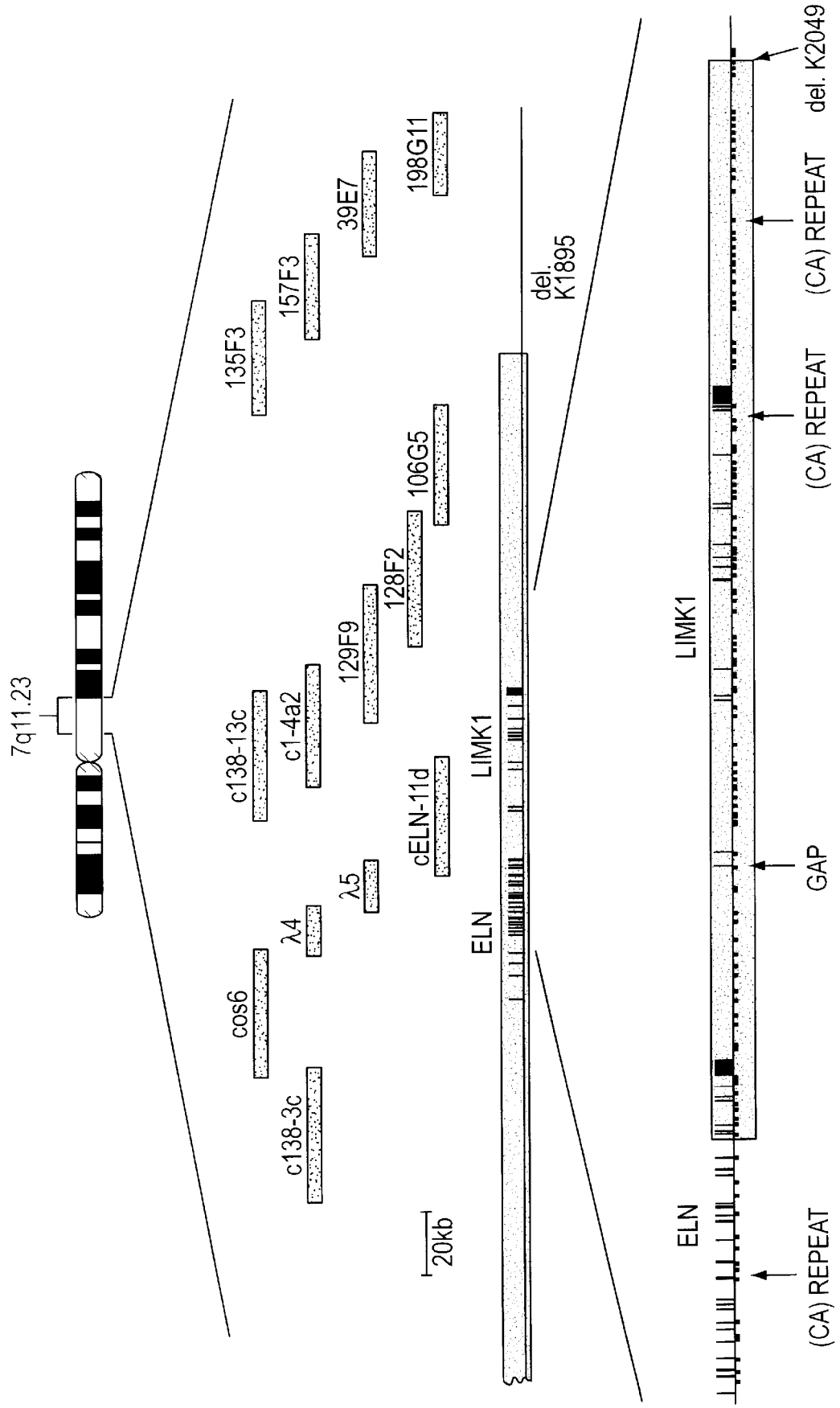
FIG. 2. Physical map of the deletions identified in K1895 and K2049. Idiogram of chromosome 7 and a contiguous set of cosmids and phage λ from chromosome 7q11.23 are shown. The relative locations and the structures of ELN and LIMK1 are indicated; exons are indicated by vertical bars extending above the horizontal lines; repetitive elements (e.g., Alu repeats) are denoted by vertical bars extending below the lower horizontal line; the locations of three d(CA)-repeats are indicated (the ELN d(CA)-repeat has been previously defined; Foster et al., 1993). The small 250 bp gap in the sequence contig is immediately 5' of LIMK1. LIMK1 is located 15.4 kb 3' of ELN and is in the same orientation. The locations of the 300 kb deletion identified in K1895 and the 83.6 kb deletion identified in K2049 are indicated by shaded boxes. Note that both deletions disrupt ELN and delete LIMK1.

Association of partial WS phenotypes with submicroscopic chromosome 7q11.23 deletions If WS is a contiguous gene deletion syndrome, individuals with a partial WS phenotype should have smaller deletions in the chromosome 7q11.23 region than those seen with classic WS. To test this hypothesis, a partial physical map of the region deleted in WS was constructed. Because ELN is completely deleted in individuals with classic WS, these experiments were initiated by isolating and characterizing ELN genomic clones. These clones were used for genomic walking into regions flanking ELN. A set of contiguous cosmid clones generated by walking 3' of ELN is shown in FIG. 2. Attempts to extend the cloned coverage in a direction 5' of ELN using phage, cosmid, P1, P1 artificial chromosomes and yeast artificial chromosome (YAC) libraries were less successful; very few clones were isolated from this region and clones that were isolated were unstable. Clones were characterized by restriction enzyme analyses and placed on the physical map by somatic cell hybrid Southern analyses or sequence-tagged-site mapping by means of the polymerase chain reaction (PCR). These clones span ~350 kb of chromosome 7q11.23, including the entire ELN locus. No other genes were previously mapped to this region.

To determine if individuals with a partial WS phenotype carried deletions involving chromosome 7q11.23, fluorescence in situ hybridization (FISH) was performed using cosmids that span the ELN locus. All affected members of K1895 showed ELN hemizygosity, while unaffected members had two ELN alleles (FIG. 1A). Additional FISH analyses revealed hemizygosity with probes c138-13c, c1-4a2, 106G5, and 135F3, but not with 157F3, 39E7, and 198G11 (data not shown). These results indicated that affected members of K1895 harbor a chromosome 7q11.23 deletion that includes ELN and extends through the locus corresponding to cosmid 135F3 (FIG. 2). Additional FISH analyses using YACs from this region are consistent with these data and indicate a deletion of approximately 300 kb (unpublished data). By contrast, FISH analyses of individuals with classic WS showed hemizygosity with all clones tested, suggesting that these deletions span more than 500 kb (unpublished data).

A deletion associated with SVAS in two members of K2049 (Ewart et al., 1994) was previously described. This deletion disrupted ELN, beginning in intron 27 and extending 3' of the gene. Oligonucleotides flanking the deletion breakpoints were used to define a novel PCR product of 403 bp in all phenotypically affected members of this kindred (FIG. 1B). This product was not seen in unaffected members. Physical mapping and restriction analyses indicated that the deletion had removed ~85 kb of genomic DNA (FIG. 2), a much smaller region than is missing in individuals with classic WS. These data indicate that a partial WS phenotype, including SVAS, some WS facial features, and WSCP, cosegregates with the ~85 kb deletion in this family. Because intragenic mutations of ELN cause isolated SVAS and some WS facial features (Curran et al., 1993; Morris et al, 1993; Olson et al, 1995), but not the WSCP (Table 1), a gene responsible for the impaired visuospatial constructive cognition must be located immediately 3' of ELN.

EXAMPLE 3
Identification of a Protein Kinase Immediately 3' of Elastin

To screen for a gene that contributes to impaired visuospatial constructive cognition, cosmids cELN-11d, c138-13c, and c1-4a2 were used in cDNA screening analyses, but no genes were identified. The specific hypothesis that hemizygosity of a gene encoding a protein kinase could cause the impaired visuospatial constructive cognition was also tested. This hypothesis was based on observations that targeted disruption of genes encoding protein kinases results in mice with impaired spatial learning (Grant et al., 1992; Abeliovich et al., 1993a, Abeliovich et al., 1993b). Oligonucleotides complementary to sequences conserved in tyrosine kinases were designed and PCR analyses were performed with genomic clones from the physical map. A specific product of 315 bp was identified from cosmid c138-13c. This PCR product was cloned; DNA sequence analyses revealed an open reading frame of 113 nucleotides with complete homology to LIM-kinasel (LIMK1), a recently identified gene encoding a protein kinase with LIM domains (Mizuno et al., 1994; Bernard et al., 1994). Oligonucleotides based on published cDNA sequences were used in PCR experiments to clone LIMK1 cDNA from a human hippocampal cDNA library. PCR analyses of DNA from somatic cell hybrids, cosmids, P1s, and YACs localized LIMK1 to the deleted region on chromosome 7q11.23. These data place LIMK1 immediately 3' of ELN and within the ~85 kb deletion identified in K2049.

Oligonucleotides based on published cDNA sequences were used in PCR experiments to clone a LIMK1 cDNA from a human hippocampal library (LIMK1 nucleotides 96–2039). A human hippocampal cDNA library (catalog #936205, Stratagene), was plated at a density of $5 \times 10^4$ pfu/15 cm plate to obtain $1 \times 10^6$ total pfu. Duplicate filters were probed with cELN-11d, c138-13c, and c1-4a2, which had been radiolabeled to a high specific activity ($>1.0 \times 10^9$ cpm/$\mu$g DNA) using random hexamer priming as described by Feinberg and Vogelstein (1984). LIMK1 cDNA fragments were obtained from the same hippocampal cDNA library using PCR with rTth DNA polymerase and various primers designed from the published LIMK1 cDNA sequence (Mizuno et al., 1994). The open reading frame (LIMK1 nucleotides 93–1936) was amplified and cloned using the following primers: 5'-ATGAGGTT GACGCTACTTTGTTGC-3' (SEQ ID NO:1) and 5'-TCAGTCGGGGACCTCAGGGTGGG C-3' (SEQ ID NO:2).

PCR primers were designed to amplify the region of homology in the kinase domains of PDGF receptor, HER2, HER3, FGF-FLG, FGF-BEK, insulin receptor, and IRR (sequences obtained from Genbank). The primers used were 5'-GACTTTGGGCTGGCTCGAGACATG C-3' (SEQ ID NO:3) and 5'-CTCCGGAGCCATCCACTTGACTGGC-3' (SEQ ID NO:4). PCR conditions were one cycle of 94° C. for 10 min, followed by 30 cycles of 94° C. for 1 min, 49° C. for 1 min, and 72° C. for 1 min, ending with one cycle of 72° C. for 10 min. Clones c138-3c, cELN-11d, and c138-13c were used as templates. Products were cloned into pBluescript II SK⁻(Stratagene) using standard T/A cloning technology (Marchuk et al., 1991) and sequenced.

Genomic clones were obtained from the following sources: c138-3c, λ4, λ5, cELN-11d, and c138-13c were derived from primary cosmid and phage libraries constructed earlier in our laboratory (Curran et al., 1993; Ewart et al., 1994). Cosmids cos6 and c1-4a2 were obtained from an amplified placental library (Stratagene). Cosmids 129F9, 128F2, 106G5, 135F3, 157F3, 39E7, and 198G11 were isolated from the chromosome 7-specific flow-sorted cosmid library constructed at the Lawrence Livermore National Laboratories.

DNA Sequence Analyses and Testing of Putative Coding Regions

Cycle sequencing with oligonucleotides generated from the LIMK1 cDNA sequence and from our DNA sequence analyses was used to define the structure of LIMK1 using cosmids cELN-11d, c138-13c, and c1-4a2. Cycle sequencing of cosmids was performed using 1.5 pmol of primer, 15 fmol of template, and the dsDNA Cycle Sequencing System (GibcoBRL). Reaction conditions were 94° C. for 3 min, 20 cycles of 94° C. for 30 s, 55° C. for 30 s, 72° C. for 1 min, 10 cycles of 94° C. for 30 s and 72° C. for 1 min. Cycle sequencing products were electrophoresed on 6% denaturing polyacrylamide gels (National Diagnostics) the same day the reactions were performed. Also, the addition of formamide to a final concentration of 4% allowed cycle sequencing of regions that could not be sequenced by standard conditions.

Sanger sequencing was performed using the Sequenase v2.0 DNA Sequencing Kit (United States Biochemical) under standard conditions. Sequence analysis relied on the IG software package and the BLAST network service from the National Center for Biotechnology Information.

Figure 3B:
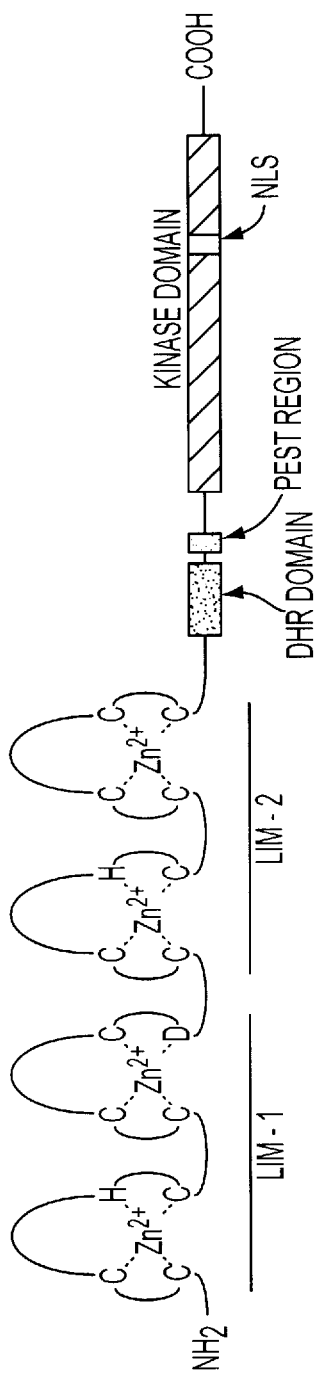

The intron-exon structure and predicted amino acid sequences are shown in Table 4 and FIG. 3. LIMK1 is composed of 16 exons, spans 37 kb, and is located 15.4 kb 3' of ELN (FIG. 2). Predicted amino acid sequence analyses revealed two putative LIM domains (amino acids 25–75 for LIM-1, 84–137 LIM-2; Way and Chalfie, 1988; Freyd et al., 1990; Karlsson et al., 1990), a Dlg homology region (DHR; amino acids 165–258; Ponting, 1995), a possible PEST domain (PESTFIND score=6.3; amino acids 264–289; Rogers et al., 1986), a kinase domain (amino acids 345–594), and a putative nuclear localization signal (NLS; amino acids 499–506; Forbes, 1992). Comprehensive DNA sequence analyses confirmed the location and structure of LIMK1.

Together, these data place LIMK1 immediately 3' of ELN and within the ~85 kb deletion identified in K2049.

were performed as described above. Four cosmids and two phage (cos6, λ4, λ5, cELN-11d, c1-4a2, and 129F9) that

TABLE 4

LIMK1 genomic structure

| Exon # | Intron | Exon Size | Intron |
|---|---|---|---|
| | ... ATGAGGTTGA (SEQ ID NO: 5) | (55)[a] | GGAGAGGAAGgtgcgcgggccgcggggcgc (SEQ ID NO: 6) |
| 2 | actcccttcccaccctgcagGAAGCGAGTT (SEQ ID NO: 7) | (97) | ACTGCTTCAGgtagggtggggtgcccaggg (SEQ ID NO: 8) |
| 3 | gcccggcccctctcctgcagGTGTTGTGAC (SEQ ID NO: 9) | (139) | ACTGGTTATGgtgagcgcccctgccttgc (SEQ ID NO: 10) |
| 4 | cctcctcacccccgcaccagGTGGCTGGGG (SEQ ID NO: 11) | (110) | AGCTGTACTGgtgagtgccttggcccctcc (SEQ ID NO: 12) |
| 5 | caccccggcggctcttgcagCGGGCACTGC (SEQ ID NO: 13) | (207) | GCGTCCAGGGgtgagtggccggcctgccga (SEQ ID NO: 14) |
| 6 | gacccctgccttacccacagAGTGGATCCG (SEQ ID NO: 15) | (106) | CCTGGACGAGgtacggtcctgagtctgtgg (SEQ ID NO: 16) |
| 7 | cacatgcctgctgtccccagATTGACCTGC (SEQ ID NO: 17) | (167) | AACCTGTCTTgtaagtcagcctgctcctcg (SEQ ID NO: 18) |
| 8 | gcaccatgtgtgccccccagGAGGAGCTGC (SEQ ID NO: 19) | (184) | GGCTATCAAGgtacagagcatgccagggtc (SEQ ID NO: 20) |
| 9 | cctctgtgtcccacacgcagGTGACACACC (SEQ ID NO: 21) | (87) | CCTCAAGGAGgtcagtgagcggaatgccct (SEQ ID NO: 22) |
| 10 | gcctgtttgtgccccgccagGTGAAGGTCA (SEQ ID NO: 23) | (132) | CAAGAGCATGgtgagtcctgggcagagcca (SEQ ID NO: 24) |
| 11 | ccattctttctccatcccagGACAGCCAGT (SEQ ID NO: 25) | (60) | ATCAGGGATGgtgagtgagccgggtgctct (SEQ ID NO: 26) |
| 12 | tcccgtgtccccgtccctagGCCTACCTCC (SEQ ID NO: 27) | (66) | GGTCCGcGAGgtgagtaccagggcccacg (SEQ ID NO: 28) |
| 13 | acccggcttcaccttcccagAACAAGAATG (SEQ ID NO: 29) | (157) | ATGATCAACGgtagtggttcagccctgccc (SEQ ID NO: 30) |
| 14 | cagtcggtctctttatccagGCCGCAGCTA (SEQ ID NO: 31) | (56) | CCTGTGCGAGgtaggtccagggttgggtag (SEQ ID NO: 32) |
| 15 | ccggggccttgtactggacagATCATCGGGC (SEQ ID NO: 33) | (158) | CCGAGAAGAGgtgagtggggtggggccctg (SEQ ID NO: 34) |
| 16 | cccacccacctgtcacccagGCCATCCTTT (SEQ ID NO: 35) | (163)[a] | CCCCGACTGA ... (SEQ ID NO: 36) |

Cosegregation of LIMK1 Hemizygosity and Impaired Visuospatial Constructive Cognition To test the hypothesis that LIMK1 hemizygosity contributes to the WSCP, FISH analyses were performed with metaphase chromosomes from individuals with both partial and classic WS phenotypes using cosmids cELN-11d, c138-13c, and c1-4a2. Cosmid probes c138-13c and c1-4a2 were labeled with biotin using a nick translation kit (GibcoBRL). Metaphase chromosome spreads were prepared from EBV transformed lymphoblastoid cell lines derived by standard procedures of colcemid arrest, hypotonic treatment and acetic acid-methanol fixation. Slides were prepared as described by Lichter et al. (1988) and hybridized with a probe mixture containing c138-13c, c1-4a2, human $C_0t$-1 DNA, and a chromosome 7-specific alpha satellite cocktail (Oncor, Inc.). For other hybridizations, cosmids 135F3, 157F3, 39E7, and 198G11 were used. Following overnight hybridization and subsequent washing, slides were incubated with streptavidin-Cy3 (cosmids) and anti-digoxigenin FITC (chromosome 7 marker). Slides were counterstained with DAPI/Antifade (Oncor, Inc.). Metaphases were scored using an epifluorescence Olympic PX50 microscope with a triple band pass filter, and then captured using a cooled CCD camera and imaging system designed specifically for FISH (Oncor, Inc.).

Figure 4A:
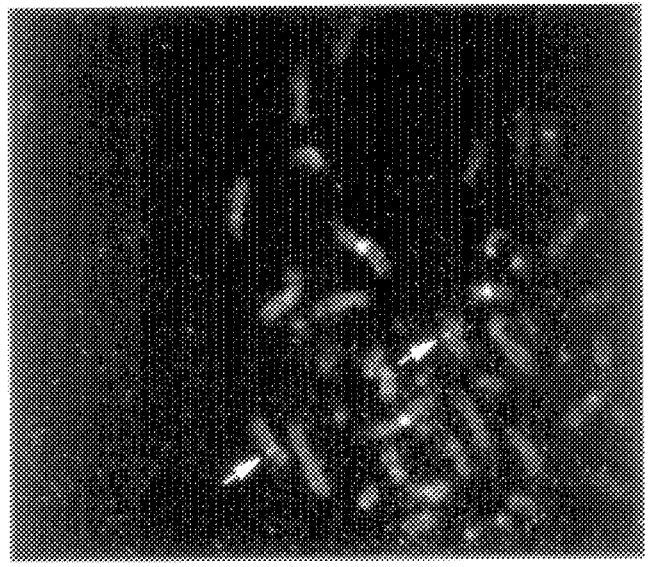
FIGS. 4A–4E. FISH analyses demonstrate hemizygosity of LIMK1 in individuals with a partial WS phenotype. Labeled LIMK1 cosmids c138-13c and c1-4a2 were hybridized with metaphase chromosomes from an affected member of K1895 (A) and of K2049 (B), an individual with classic WS (C), an individual with SVAS with a translocation disrupting ELN in exon 28 (D), and an individual with SVAS and no chromosomal anomaly (E). Centromere-specific markers are indicated by arrows (chromosome 7 for all individuals and chromosomes 6 and 7 for the translocation). Affected members of K1895, K2049, and classic WS individuals showed LIMK1 hemizygosity. The individual with SVAS and a t(6p21;7q11) translocation showed hybridization signals on the normal homologue, as well as on the 7q:6q translocation chromosome. An individual with SVAS, with no chromosomal abnormalities, showed LIMK1 hybridization signals on both chromosome 7 homologues. All individuals showed two hybridization signals for chromosome 7 centromere-specific marker.
Figure 4B:
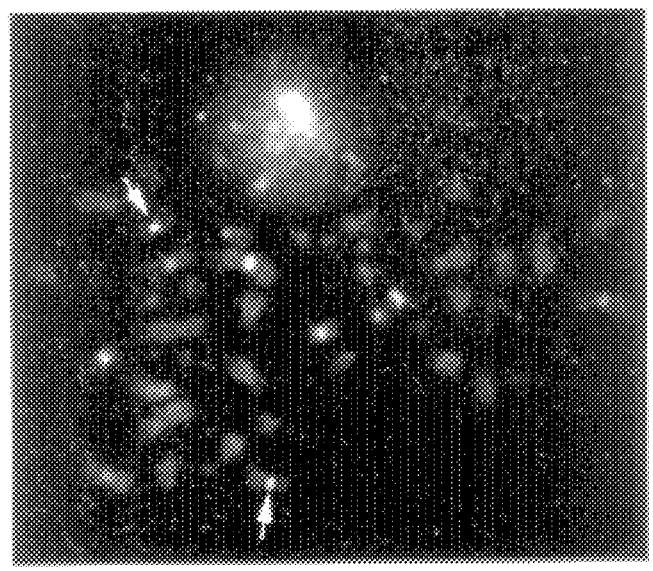
Figure 4C:
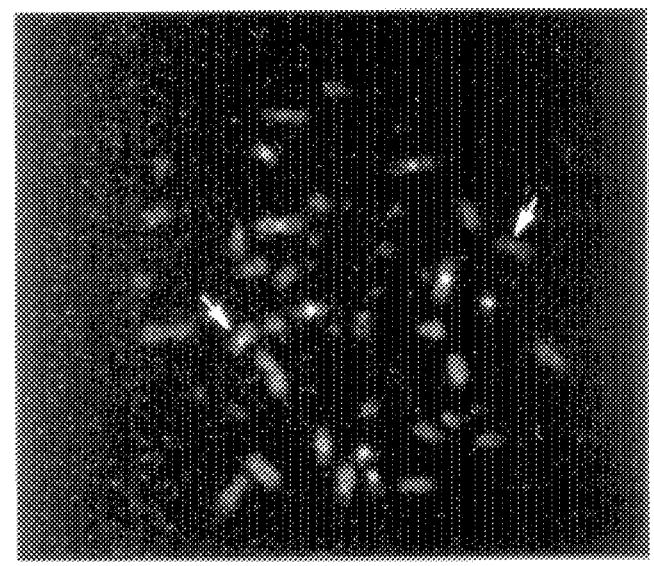
Figure 4D:
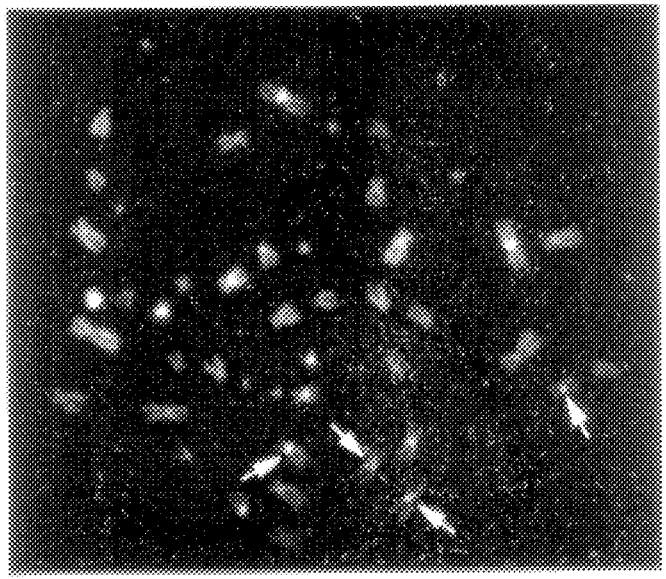
Figure 4E:
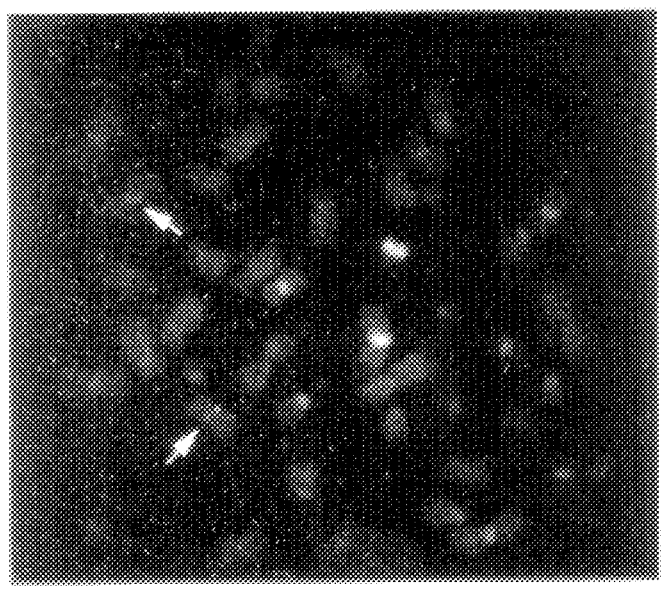

LIMK1 was completely deleted from one chromosome 7 homologue in affected members of K1895 and K2049 and in 62 of 62 individuals with classic WS (e.g., FIG. 4A–4C). LIMK1 was not deleted in 6 of 6 individuals with isolated and de novo SVAS who showed some WS facial features (e.g., FIG. 4D). LIMK1 hemizygosity was not observed among more than 100 control individuals (FIG. 4E and data not shown). These data indicate that LIMK1 is deleted in individuals with classic and partial WS but not in individuals with isolated SVAS, and suggest that LIMK1 hemizygosity contributes to the WSCP.

EXAMPLE 4

Direct DNA sequence analysis of the ~85 kb deletion region reveals only LIMK1 and ELN To determine if LIMK1 is the only gene from this region likely to contribute to cognitive development, the ~85 kb segment deleted in K2049, along with flanking sequences, was sequenced. Cycle sequencing and Sanger sequencing form an overlapping contig of the entire 83.6 kb deletion region in K2049 and the flanking sequences surrounding the breakpoints were sequenced. A modification of the sequencing procedure described by Mardis (1994) was used. Approximately 900 single-stranded M13 clones were sequenced for each cosmid using dye-primer chemistry (Applied Biosystems, Epicentre Technologies, and Amersham). Products from the sequencing reactions were run on either an ABI 373a Stretch DNA Sequencer or an ABI 377 Prism DNA Sequencer. The sequence data were processed using the XGAP algorithms (Dear and Staden, 1991; Dear and Staden, 1992). Gaps in the 83.6kb contig were filled in by one of the following methods: 1) direct sequencing of cosmids using specific primers; 2) sequencing of PCR products generated using primers that flank the gaps; or 3) subcloning restriction fragments containing the gaps into pBluescript II SK⁻(Stratagene) and sequencing them using dye-primers.

The 83.6-kb sequence was analyzed for known genes using GENQUEST and BLAST servers. Potential coding exons, polyadenylation sites, and CpG islands were identified by versions 1.2 and 2 of the GRAIL neural network. All putative coding regions with either excellent or good scores were tested for mRNA expression by either Northern-blot analysis (human MTN blot 1 and human fetal MTN blot) or a combination of Northern-blot analysis and RT-PCR.

RT-PCR was performed according to manufacturer's instructions using 200 ng of total RNA and the Thermostable rTth Reverse Transcriptase RNA PCR kit (Perkin Elmer). Controls included 100 ng of genomic DNA, 100 ng of genomic DNA that had been digested with 10 units of DNAse I, and a water blank. RNA samples were prepared with and without DNAse I treatment. Reverse transcription was performed for 15 minutes at 60° C. PCR was performed for either 35 or 50 cycles on a Perkin Elmer 9600 GeneAmp PCR System using the following cycling conditions: 1) initial denaturation at 94° C. for 3 minutes; 2) subsequent denaturation at 95° C. for 10 seconds; 3) annealing and extension at 60° C. for 15 seconds. Products were electrophoresed through a 5% 3:1 agarose gel (FMC) and visualized by staining with ethidium bromide.

DNA sequence analyses defined two ordered contigs of 41,566 and 65,607 base pairs. These contigs were separated by a gap of approximately 250 base pairs (FIG. 2). Due to its high GC content, this gap could not be sequenced using primer walking, amplified PCR products, or subcloning. The restriction maps predicted from DNA sequence analyses were identical to maps generated using BamHI, EcoRI, and HindIII. The size of the deletion was 83.6 kb. The sequences were analyzed for the presence of known genes using the GRAIL, GENQUEST, and BLAST servers (Shah et al., 1994; Altschul et al., 1990). Only ELN and LIMK1 were detected.

Comparison between the cDNA and genomic sequence revealed 16 LIMK1 exons that span 37 kb of genomic DNA. Sequence analyses also indicated that LIMK1 is located 15.4 kb 3' of ELN (FIG. 2). Predicted amino acid sequence analyses identified all previously described domains including LIM-1, LIM-2, a Dlg homology region, a putative nuclear localization signal, and a kinase domain (Mizuno et al., 1994; Ponting, 1995). In addition, sequence analyses revealed a possible PEST domain (PESTFIND score=6.3; amino acids 264–289; Rogers et al., 1986).

Sequences were also scanned for potential coding regions using versions 1.2 and 2 of the GRAIL neural network (Table 5). Except for ELN (GRAIL identified 16 of 30 exons) and LIMK1 (15 of 16 exons), no other putative exons categorized as excellent were identified by GRAIL. Additionally, GRAIL identified seven possible coding sequences categorized as good (six within the 83.6 kb deletion region) and eleven categorized as marginal. All possible coding sequences classified as good were tested using either multiple-tissue Northern analyses or a combination of Northern analyses and reverse transcription-PCR of total RNA extracted from fetal and adult human brain (Table 5 and data not shown). No evidence for expression of these additional possible coding sequences was found.

A remarkable finding of DNA sequence analyses was the high density of Alu repetitive elements in the 83.6 kb deletion region. A total of 120 full or partial Alu sequences was identified, for an average density of ~1.4/kb. This is 6-fold more than the estimated average density of 0.25/kb (Hwu et al., 1986; Slightom et al., 1994). One partial LINE sequence and one MER14-like element were also identified, as well as three large d(CA)-repeats (FIG. 2). One of the d(CA)-repeats had been previously identified (Foster et al., 1993). Sequence analyses also defined the breakpoints for the K2049 deletion; both breakpoints consisted of Alu repeats, suggesting that a recombination event between these Alu sequences may have been responsible for the deletion.

TABLE 5

GRAIL Analyses of DNA Sequences within the 83.6 kb Deleted Region

| Putative Coding Region | Size (bp) | Grail Version | Grail Quality | Strand (F/R) | Exclusion |
|---|---|---|---|---|---|
| ELN-29 | 60 | 1.2 | E | F | — |
| ELN-30 | 75 | 1.2,2 | E | F | — |
| 208pr3 | 114 | 1.2 | G | R | N,RP |
| 124pr3 | 85 | 1.2 | G | R | N,RP |
| 90pr1 | 123 | 1.2 | G | R | N,RP |
| LIMK-2 | 97 | 1.2,2 | E | F | — |
| 441pr1 | 141 | 1.2,2 | G | F | N,RP |
| LIMK-3 | 139 | 1.2,2 | E | F | — |
| LIMK-4 | 110 | 1.2,2 | E | F | — |
| LIMK-5 | 207 | 1.2,2 | E | F | — |
| LIMK-6 | 106 | 1.2,2 | E | F | — |
| LIMK-7 | 167 | 1.2,2 | E | F | — |
| LIMK-8a | 36 | 2 | E | F | — |
| LIMK-8b | 123 | 1.2,2 | E | F | — |
| LIMK-9 | 87 | 1.2,2 | E | F | — |
| LIMK-10 | 132 | 1.2,2 | E | F | — |
| LIMK-11 | 60 | 2 | G | F | — |
| LIMK-12 | 66 | 1.2,2 | E | F | — |
| 604pr2 | 39 | 2 | G | F | N,* |
| LIMK-13 | 157 | 1.2,2 | E | F | — |
| LIMK-14 | 56 | 1.2,2 | G | F | — |
| LIMK-15 | 158 | 1.2,2 | E | F | — |
| LIMK-16 | 163 | 1.2,2 | E | F | — |
| 604pr3 | 31 | 2 | G | R | N,* |

Table 5. Only the putative coding regions with either excellent or good scores are listed in this table. The putative coding regions are either named after the gene and exon number (e.g., ELN-29 is exon 29 of the elastin gene) or given an assigned name (e.g., 208pr3). Putative exons are given either excellent (E) or good (G) scores. F=forward strand in relation to ELN and LIMK; R=reverse strand. N=no evidence for expression by Northern blot analysis; RP=no evidence for expression by RT-PCR; *=putative coding region not tested by RT-PCR because the coding region was too short; -=not tested because the putative coding region is an exon of a known gene.

EXAMPLE 5
LIMK1 and ELN Expression in the Developing Brain

To determine the expression pattern of LIMK1, Northern analyses were performed with mRNA extracted from fetal and adult tissues. Northern blots containing ~2 μg/lane of poly(A)+ mRNA were purchased from Clonetech (human MTN blot 1, human brain blots 2 and 3, human fetal MTN blot, and a mouse MTN blot). The blots were hybridized in ExpressHyb solution (Clonetech) according to the manufacturer's instruction, with either $^{32}$P-end-labeled LIMK1 oligonucleotide probe (704–742 bp) or LIMK1 (104–2038 bp), ELN (1–1123 bp), and β-actin cDNA clones that had been radiolabeled using random hexamer priming (Feinberg and Vogelstein, 1984). Each LIMK1 Northern blot was analyzed by phosphorimage analyses (Molecular Dynamics) to determine the amounts of LIMK1 RNA relative to β-actin mRNA.

Figures 5A, 5B:
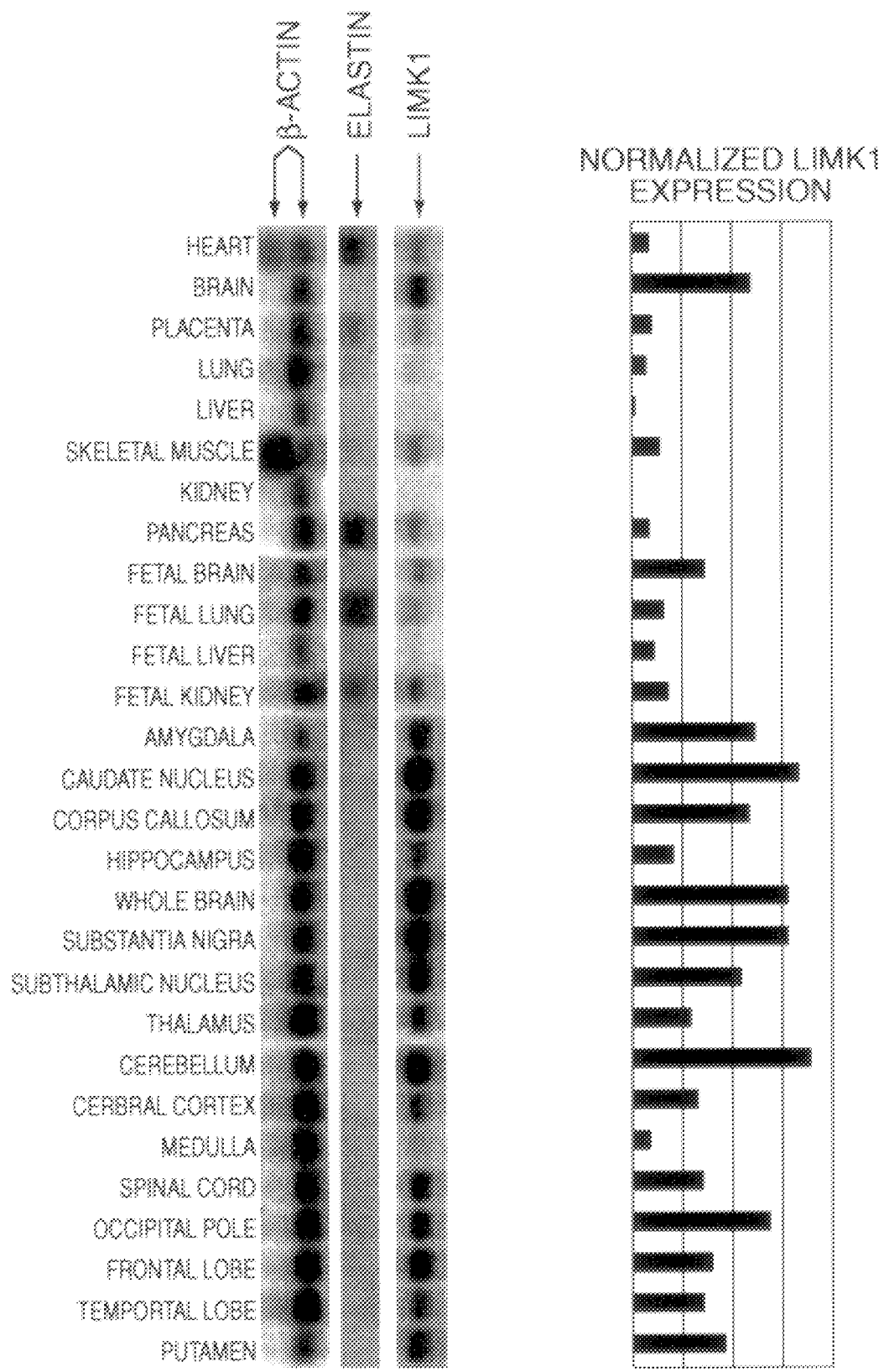
FIGS. 5A–5B. LIMK1 is expressed strongly in the brain.
Figure 6A:
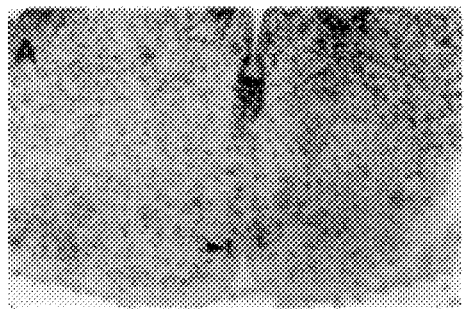
FIGS. 6A–6H. In situ hybridization analysis of LIMK1 expression in the nervous system of a Carnegie stage 20 (50 day postovulatory) human embryo. A 625-bp LIMK1 cRNA probe was labeled with DIG-UTP and visualized using anti-DIG alkaline phosphatase antibody. (A) Transverse section through rhombencephalon/medulla, fourth ventricle. LIMK1 expression is seen in the ependymal layer of the fourth ventricle and a lower level of expression extends into the mantle layer. The arrow indicates expression in the medial accessory olivary nucleus on either side of the midline; this area is shown in greater detail in C. (B) Similar section to (A) hybridized with the sense-strand cRNA probe as a negative control. (C) Medial accessory olivary nuclei shown in the center of (A). (D) Transverse section through the cerebellum (c) showing a high level of ependymal expression in the corpus cerebelli (fourth ventricle on the right and ectoderm on the left). Some expression is visible in the mesenchyme adjacent to the ectoderm, in particular in the presumptive dentate nucleus (arrow). (E) Transverse section through the cervical spinal cord showing generalized expression in the dorsal (top) part of the spinal cord and single-cell staining more ventrally (right). There is also expression in the dorsal root ganglia (d). (F) Section through the wall of the mesencephalon (the ventricle is on the far right); the ependymal layer is on the right and heavily stained, and the mantle layer in the center-left shows many cells expressing LIMK1. An arrow indicates the sulcus limitans. (G) Higher magnification of (E), showing the mid-area of the spinal cord, demonstrates a low level of confluent expression in the ependymal layer (right), widespread single-cell staining in the mantle layer (center), and lack of expression in the marginal layer (left). (H) Transverse section through the fifth nerve ganglion shows high expression in the center, in part of the inner ear (lower right, below the scale bar), and in the ectoderm (left). The scale bar represents either 100 μm (C, F, and G) or 250 μm (A, B, D, E, and H).
Figure 6B:
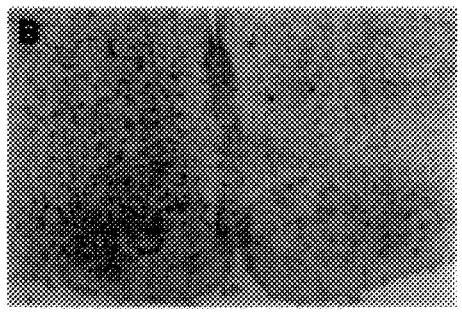
Figure 6C:
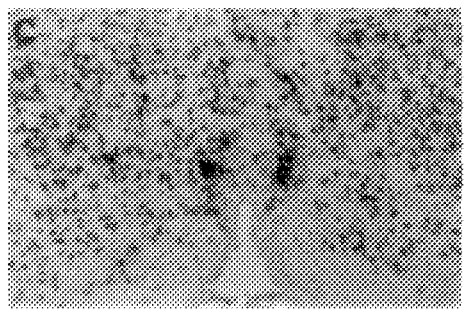
Figure 6D:
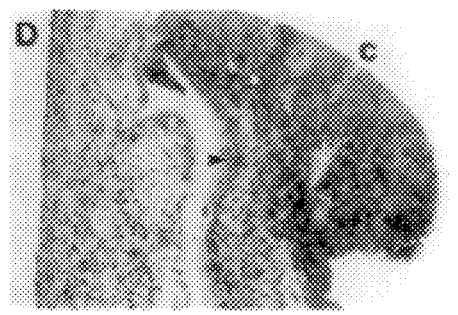
Figure 6E:
Figure 6F:
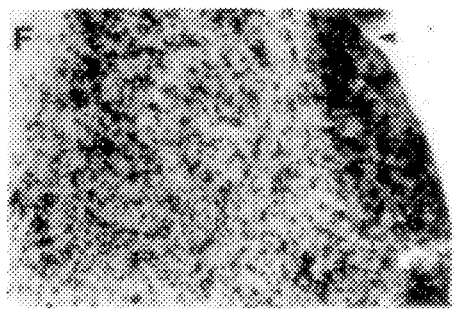
Figure 6G:
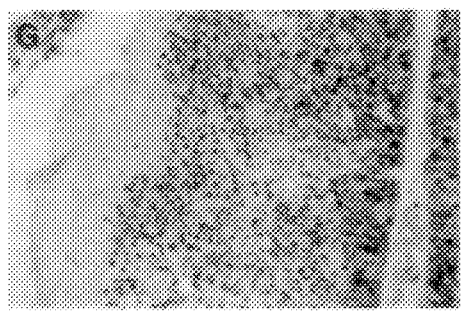
Figure 6H:
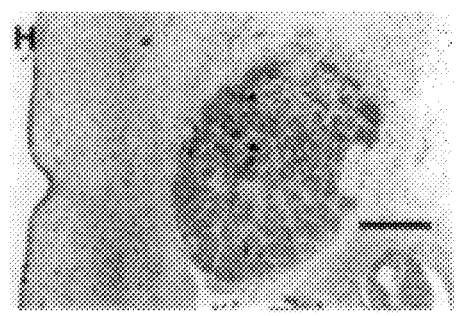

A LIMK1 oligonucleotide probe hybridized to a single mRNA of 3.3 kb in all fetal and adult tissues examined (FIG. 5). Phosphorimage analyses indicated that mRNA levels varied considerably but were highest in both fetal and adult brain. Northern analyses of tissue from different regions of the adult human brain demonstrated that LIMK1 is ubiquitously expressed, with mRNA levels highest in the cerebellum, caudate nucleus, substantia nigra, and the occipital pole (FIG. 5). Analyses of adult murine tissues indicated that LIMK1 is most strongly expressed in testes and brain (data not shown). These data establish that LIMK1 is widely expressed during fetal and adult life, but that LIMK1 mRNA levels are highest in the brain.

In situ hybridization analyses of LIMK1 expression in the embryonic human nervous system demonstrated that LIMK1 is expressed in several discrete regions of the brain and spinal cord (FIG. 6). In situ hybridization was performed on 6 mm-thick, paraffin embedded sections of freshly prepared human embryos, which were obtained from the MRC-funded Human Embryonic Tissue Bank, Institute of Child Health, London. A digoxigenin-labeled 625-bp cRNA probe specific to the 3'-untranslated portion of LIMK1 cDNA was used to avoid areas of homology with other genes encoding proteins containing LIM and kinase domains; similar results were obtained, however, in some sections hybridized with a cDNA probe covering the kinase region and some of the 3'-untranslated sequence. The in situ protocol was based on the detection of digoxigenin-labeled RNA by alkaline phosphatase-conjugated anti-DIG FAB fragments (Boehringer Mannheim), as previously described (Wilkinson, 1992; Birren et al., 1993). Brightfield microphotography was carried out with an Olympus BH-2 and Fujichrome 64T film.

Analyses of LIMK1 expression in a Carnegie stage 20 (postovulatory day 50) human embryo revealed expression in the ependymal layer of the fourth ventricle, with a lower level of expression extending into the mantle layer. LIMK1 was expressed in specific regions of the brain, with notably high levels in the medial olivary nucleus. In the cerebellum, expression was seen again in ependymal layer. Staining also occurred in ependymal layer of the mesencephalon, which additionally contained many LIMK1-expressing cells in the mantle layer. In the spinal cord, LIMK1 was expressed in a diffuse pattern dorsally, with single-cell staining ventrally. In the mid-area of the spinal cord, expression was again seen in ependymal and mantle layers. Within the peripheral nervous system, extensive expression of LIMK1 was seen in spinal ganglia, in the fifth nerve ganglion, and in part of the inner ear.

To determine if ELN is expressed in the brain, Northern analyses were performed with mRNA extracted from fetal and adult tissues. ELN was strongly expressed in adult heart and pancreas and in fetal lung, but exhibited negligible expression in adult and fetal brain.

EXAMPLE 6

Distinguishing between SVAS. WSCP and WS

Supravalvular aortic stenosis (SVAS), Williams syndrome cognitive profile (WSCP) and Williams syndrome are inherited diseases which are related in that they involve a set of contiguous genes. Persons with mutations in the elastin gene but who are wild-type for LIMK1 and do not have deletions 3' of LIMK1 have SVAS. Persons who have mutations affecting both elastin and LIMK1 (hemizygosity) but do not have deletions greater than about 300 kb 3' of the ELN gene are diagnosed as having WSCP. Persons who are mutated in both the ELN and LIMK1 genes (and have one wild-type copy of each of these genes) and have a deletion of greater than 300 kb from the 3' end of the LIMK1 gene in the 3' direction are diagnosed as having WS. One may conclude that SVAS is due to a mutation in or loss of a single gene (ELN), WSCP is a result of mutations in or loss of two genes (ELN and LIMK1), and WS results from mutations in or a loss of at least 3 genes (ELN, LIMK1 and an unidentified gene or genes located on chromosome 7 greater than 300 kb 3' of LIMK1). It is possible to diagnose which disease a patient may have by use of chromosomal analysis. The complete sequence of the elastin and LIMK1 cDNAs have been published (Indik et al., 1987; Fazio et al., 1988; Mizuno et al., 1994; Cheng and Robertson, 1995). SEQ ID NO:39 shows a cDNA sequence of elastin (from Fazio et al., 1998 and Indik et al., 1987) and SEQ ID NO:40 shows the amino acid sequence encoded by this cDNA sequence. SEQ ID NO:41 Shows a cDNA sequence for LIMK1 (from Mizuno et al., 1994). SEQ ID NO:42 shows the amino acid sequence encoded by SEQ ID NO:41. Using the known nucleic acid sequences for these two genes it is possible to assay for mutations in these genes. This can be done by any desired technique such as by sequencing to determine the presence of mutations, especially the presence of deletions or translocations affecting the genes, or by in situ hybridization to determine whether these genes are hemizygous or homo- or heterozygous. Using the knowledge of these two genes one can assay to determine if the patient has at least SVAS (i.e., loss of or mutation in at least ELN), or at least WSCP (loss of or mutation in both ELN and LIMK1). To determine whether an individual has WS it is helpful to examine the chromosome beyond the 3' ends of ELN and LIMK1. To date, all Williams syndrome patients analyzed have been found to have a major deletion in chromosome 7 which includes deletion of both the ELN (at least partially) and LIMK1 genes as well as greater than another 300 kb 3' of the LIMK1 gene. Patients who have deletions of 100 kb or smaller 3' of the LIMK1 gene have been diagnosed as having WSCP but not WS. The use of probes to analyze for the extent of deletion of chromosome 7 in individuals can distinguish between WSCP and WS.

FIG. 2 shows a map of chromosome 7 in the region of ELN and LIMK1 with a series of overlapping cosmids covering this region. The range of coverage from c138-3c through 198G11 is approximately 350 kb. In situ hybridization with 135F3, for example, can be used to determine if there is a deletion of 100 kb or less 3' of LIMK1. If 135F3 hybridizes to both sets of chromosomes then the individual probably will not have WS since the deletion will be too small to delete the third, as yet unknown, gene which lies 3' of ELN and LIMK1 and which must be mutated or deleted to cause WS. To date, all WS individuals have been found to have a deletion greater than 500 kb covering ELN and LIMK1 and greater than 300 kb 3' of LIMK1. Furthermore, it has been seen that when a person does have a deletion in ELN there is a 99% chance that this is a major deletion of greater than 500 kb including LIMK1 and the other gene or genes involved in WS. This means that the presence of a deletion in ELN in one chromosome is 99% indicative of the presence of WS.

While the invention has been disclosed in this patent application by reference to the details of preferred embodiments of the invention, it is to be understood that the disclosure is intended in an illustrative rather than in a limiting sense, as it is contemplated that modifications will readily occur to those skilled in the art, within the spirit of the invention and the scope of the appended claims.

LIST OF REFERENCES

Abeliovich, A., Chen, C., Goda, Y., Silva, A. J., Stevens, C. F., & Tonegawa, S. (1993a). Modified hippocampal long-term potentiation in PKCγ mutant mice. Cell 75, 1253–1262.

Abeliovich, A., Paylor, R., Chen, C., Kim, J. J., Wehner, J. M., & Tonegawa, S. (1993b). PKCγ mutant mice exhibit mild deficits in spatial and contextual learning. Cell 75, 1263–1271.

Altschul, F. F., Gish, W., Miller, W., Myers, E. W., and Lipman, D. J. (1990). Basic local alignment search tool. J. Mol. Biol. 215, 403–410.

Bayley, N. (1969). Bayley Scales of Infant Development. (New York, N.Y.: Psychological Corporation).

Bayley, N. (1993). Bayley Scales of Infant Development (2nd ed.) (San Antonio, Tex.: Psychological Corporation).

Beery, K. E. (1989). Developmental Test of Visual Motor Integration (3rd revision). (Cleveland, Ohio: Modern Curriculum Press).

Bellugi, U., Wang, P. P., & Jernigan, T. L. (1994). Williams syndrome: An unusual neuropsychological profile. In Atypical Cognitive Deficits in Developmental Disorders: Implications for Brain Function. S. H. Broman & J. Grafman, eds. (Hillsdale, N.J.: Erlbaum), pp. 23–56.

Bernard, O., Ganiatsas, S., Kannourakis, G., & Dringen, R. (1994). Kiz-1, a protein with LIM zinc finger and kinase domains, is expressed mainly in neurons. Cell Growth & Dif. 5, 1159–1171.

Birren, S. J., Lo, L., and Anderson, D. J. (1993). Sympathetic neuroblasts undergo a developmental switch in trophic dependence. Development 119, 597–610.

Budarf, M. L., Collins, J., Gong, W., Roe, B., Wang, Z., Bailey, L. C., Sellinger, B., Michaud, D., Driscoll, D. A., and Emanuel, B. S. (1995). Cloning a balanced translocation associated with DiGeorge syndrome and identification of a disrupted candidate gene. Nat. Genet. 10, 269–278.

Capruso, D. X., Hamsher, K., Benton, A. L. (1995). Assessment of visuocognitive processes. In *Clinical Neuropsychological Assessment: A Cognitive Approach.* R. L. Mupou and J. Spector (eds.) (New York: Plenum), pp. 137–183.

Cheng, A. K., and Robertson, E. J. (1995). The murine LIM-kinase gene (limk) encodes a novel serine threonine kinase expressed predominantly in trophoblast giant cells and the developing nervous system. Mech. Dev. 52, 187–197.

Curran, M. E., Atkinson, D. L., Ewart, A. K., Morris, C. A., Leppert, M. F., and Keating, M. T. (1993). The elastin gene is disrupted by a translocation associated with supravalvular aortic stenosis. Cell 73, 159–168.

Curran, M. E., Splawski, I., Timothy, K. W., Vincent, G. M., Green, E. D., and Keating, M. T. (1995). A molecular basis for cardiac arrhythmia: HERG mutations cause long QT Syndrome. Cell 80, 795–803.

Dear, S., and Staden, R. (1991). A sequence assembly and editing program for efficient management of large projects. Nucl. Acids Res. 19, 3907–3911.

Dear, S., and Staden, R. (1992). A standard file format for data from DNA sequencing instruments. DNA Seq. 3, 99–105.

Dilts, C. V., Morris, C. A., and Leonard, C. 0. (1990). Hypothesis for development of a behavioral phenotype in Williams syndrome. Am. J. Med. Genet. Suppl. 6, 126–131.

Elliott, C. D. (1990). Differential Ability Scales. (San Diego, Calif.: Harcourt Brace Jovanovich).

Ensing, G. J., Schmidt, M. A., Hagler, D. J., Michels, V. V., Carter, G. A., and Feldt, R. H. (1989). Spectrum of findings in a family with nonsyndromic autosomal dominant supravalvular aortic stenosis: A Doppler echocardiographic study. J. Am. Coll. Cardiol. 13, 413–419.

Ewart, A. K., Jin, W., Atkinsin, D. L., Morris, C. A., & Keating, M. T. (1994). Supravalvular aortic stenosis associated with a deletion disrupting the elastin gene. J. Clin. Invest. 93, 1071–1077.

Ewart, A. K., Morris, C. A., Atkinson, D. L., Jin, W., Sternes, K., Spallone, P., Stock, D., Leppert, M., and Keating, M. T. (1993a). Hemizygosity at the elastin locus in a developmental disorder, Williams syndrome. Nat. Genet. 5, 11–16.

Ewart, A. K., Morris, C. A., Ensing, G. J., Loker, J., Moore, C., Leppert, M., and Keating, M. T. (1993b). A human vascular disorder, supravalvular aortic stenosis, maps to chromosome 7. Proc. Natl. Acad. Sci. USA 90, 3226–3230.

Fazio, M. J., Olsen, D. R., Hauh, E. A., Baldwin, C. T., Indik, Z., Ornstein-Goldstein, N., Yeh, H., Rosenbloom, and Uitto, J. (1988). Cloning of Full-length Elastin cDNAs from a Human Skin Fibroblast Recombinant cDNA Library: Further Elucidation of Alternative Splicing Utilizing Exon-specific Oligonucleotides. J. Investigative Dermatology 91:458464.

Feinberg, A., and Vogelstein, B. (1984). A technique for radiolabeling DNA restriction endonuclease fragments to high specific activity. Anal. Biochem. 137, 266–267.

Forbes, D. J. (1992). Structure and function of the nuclear pore complex. Ann. Rev. Cell Biol. 8, 495–527.

Foster, K., Ferrell, R., King-Underwood, L., Povey, S., Attwood, J., Rennick, R., Humphries, S. E., and Henney, A. M. (1993). Description of a dinucleotide repeat polymorphism in the human elastin gene and its use to confirm assignment of the gene to chromosome 7. Ann. Hum. Genet. 57, 87–96.

Freyd, G., Kim, S. K., and Horvitz, H. R. (1990). Novel cysteine-rich motif and homeodomain in the product of the *Caenorhabditis elegans* cell lineage gene lin-11. Nature 344, 876–879.

Gilbert-Dussardier, B., Bonneau, D., Gigarel, N., Merrer, M. L., Bonnet, D., Philip, N., Serville, F., Verloes, A., Rossi, A., Ayme, S., Weissenbach, J., Mattei, M. G., Lyonnet, S., and Munnich, A. (1995). A novel microsatellite DNA marker at locus D7S1870 detects hemizygosity in 75% of individuals with Williams syndrome. Am. J. Hum. Genet 56, 542–544.

Grant, S. G. N., O'Dell, T. J., Karl, K. A., Stein, P. L., Soriano, P., and Kandel, E. R. (1992). Impaired long-term potentiation, spatial learning, and hippocampal development in fyn mutant mice. Science 258, 1903–1910.

Grimm, T. & Wesselhoeft, H. (1980). Zur genetic des Williams-Beuren syndrome und der isolierten form der supravalvularen aortenstenose: untersuchungen von 128 familien. Z. Kardiol. 69, 168–172.

Hanks, S. K., Quinn, A. M., and Hunter, T. (1988). The protein kinase family: conserved features and deduced phylogeny of the catalytic domains. Science 241, 42–52.

Hwu, H. R., Roberts, J. W., Davidson, E. H., and Britten, R. J. (1986). Insertion and/or deletion of many repeated DNA sequences in human and higher ape evolution. Proc. Natl. Acad. Sci. USA 83, 3875–3879.

Indik, Z., Yeh, H., Ornstein-Goldstein, N., Sheppard, P. Anderson, N., Rosenbloom, J. C., Peltonen, L. and Rosenbloom, J. (1987). Alternative splicing of human elastin mRNA indicated by sequence analysis of cloned genomic and complementary DNA. Proc. Natl. Acad. Sci. USA 84:5680–5684.

Karlsson, O., Thor, S., Norberg, T., Ohlsson, H., and Edlund, T. (1990). Insulin gene enhancer binding protein Isl-1 is a member of a novel class of proteins containing both a homeo and a Cys-His domain. Nature 344, 879–882.

Kozak, M. (1989). The scanning model for translation: an update. J. Cell Biol. 108, 229–241.

Lichter, P., Cremer, T., Borden, J., Manuelidis, L., and Ward, D. C. (1988). Delineation of individual human chromosomes in metaphase and interphase cells by in situ suppression hybridization using recombinant DNA libraries. Human Genet. 80, 224–234.

Lowery, M. C., Morris, C. A., Ewart, A., Brothman, L. J., Zhu, X. L., Leonard, C. O., Carey, J. C., Keating, M., and Brothman, A. R. (1995). Strong correlation of elastin deletions, detected by FISH, with Williams syndrome: evaluation of 235 patients. Am. J. Hum. Genet. 57, 49–53.

Marchuk, D., Drumm, M., Saulino, A., and Collins, F. S. (1991). Construction of T-vectors, a rapid and general system for direct cloning of unmodified PCR products. Nucleic Acids. Res. 19, 1154.

Mardis, E.R. (1994). High-throughput detergent extraction of M13 subclones for fluorescent DNA sequencing. Nucleic Acids Res. 22, 2173–2175.

Mervis, C. B. and Bertrand, J. (in press). Relations between cognition and language: A developmental perspective. In Research on Communication and Language Disorders: Contributions to Theories of Language Development, L. B. Adamson and M. A. Romski, eds. (New York, N.Y.: Brookes).

Mervis, C. B., Morris, C. A., Bertrand, J., and Robinson, B. F. (in press). Williams syndrome: Findings from an Integrated Program of Research. In Neurodevelopmental Disorders: Contributions to a New Framework from the Cognitive Neurosciences. H. Tager-Flusberg, ed. (Cambridge, Mass.: MIT Press).

Mizuno, K., Okano, I., Ohashi, K., Nunoue, K., Kuma, K., Miyata, T., and Nakamura, T. (1994). Identification of a human cDNA encoding a novel protein kinase with two repeats of the LIM/double zinc finger motif. Oncogene 9, 1605–1612.

Morris, C. A., Dilts, C., Demsey, S. A., Leonard, C. O., and Blackburn, B. (1988). The natural history of Williams syndrome: physical characteristics. J. Pediatr. 113, 318–326.

Morris, C. A., Loker, J., Ensing, G., and Stock, A. D. (1993). Supravalvular aortic stenosis cosegregates with a familial 6;7 translocation which disrupts the elastin gene. Am. J. Med. Genet. 46, 737–744.

Nunoue, K., Ohashi, K., Okano, I., and Mizuno, K. (1995). LIMK-1 and LIMK-2, two members of a LIM motif-containing protein kinase family. Oncogene 11, 701–710.

Olson, T. M., Michels, V. V., Urban, Z., Csiszar, K., Christiano, A. M., Driscoll, D. J., Feldt, R. H., Boyd, C. D., and Thibodeau, S. N. (1995). A 30 kb deletion within the elastin gene results in familial supravalvular aortic stenosis. Hum. Mol. Genet. 4, 1677–1679.

Ponting, C. P. (1995). DHR domains in syntrophins, neuronal NO synthases and other intracellular proteins. Trends Biol. Sci. 20, 102–103.

Pröschel, C., Blouin, M.-J., Gutowski, N. J., Ludwig, R., and Noble, M. (1995). Limk1 is predominantly expressed in neural tissues and phosphorylates serine, threonine and tyrosine residues in vitro. Oncogene 11, 1271–1281.

Preus, M. (1984). The Williams syndrome: Objective definition and diagnosis. Clin. Genet. 25, 422–428.

Rogers, S., Wells, R., and Rechsteiner, M. (1986). Amino acid sequences common to rapidly degraded proteins: the PEST hypothesis. Science 234, 364–368.

Schmeichel, K. L., and Beckerle, M. C. (1994). The LIM domain is a modular protein-binding interface. Cell 79, 211–219.

Shah, M. B., Guan, X., Einstein, J. R., Matis, S., Xu, Y., Mural, R. J. and Uberbacher, E. C. (1994). User's guide to GRAIL and GENQUEST (Sequence analysis, gene assembly and sequence comparison systems) E-mail servers and XGRAIL (version 1.2) and XGENQUEST (version 1.1) client-server systems. Available by anonymous ftp to arthur.epm.oml.gov from directory pub/xgrail as file Manual.grail-genquest.July94.

Shapiro, M. B. and Senapathy, P. (1987). RNA splice junctions of different classes of eukaryotes: sequence statistics and functional implications in gene expression. Nucleic Acids Res. 15, 7155–7174.

Slightom, J. L., Siemieniak, D. R., Sieu, L. C., Koop, B. F., and Hood, L. (1994). Nucleotide sequence of 77.7 kb of the human $V_\beta$ T-cell receptor gene locus: direct primer-walking using cosmid template DNAs. Genomics 20, 149–168.

Udwin, O., Yule, W., and Martin, N. (1987). Cognitive abilities and behavioral characteristics of children with idiopathic infantile hypercalcemia. J. Child. Psychology and Psychiatry 28, 297–309.

Way, J. C., and Chalfie, M. (1988). mec-3, a homeobox-containing gene that specifies differentiation of the touch receptor neurons in C. elegan. Cell 54, 5–16.

Wechsler, D. (1981). Wechsler Adult Intelligence Scale-Revised. (San Antonio, Tex.: Psychological Corporation).

Wilkinson, D. G. (1992). In Situ Hybridisation: A Practical Approach. IRL Press, Oxford.

---

What is claimed is:

1. A method for determining the presence of impaired visuospatial constructive cognition, said method comprising determining zygosity in an individual of LIM-kinase 1 (LIMK1), wherein a nucleic acid probe or primer specific for LIMK1 is hybridized to said individual's nucleic acid, wherein hemizygosity of LIMK1 is indicative of impaired visuospatial constructive cognition.

2. The method of claim 1 wherein said zygosity is measured by in situ hybridization.

3. The method of claim 1 wherein said zygosity is measured by fluorescent in situ hybridization.

4. The method of claim 1 wherein said zygosity is measured using a polymerase chain reaction.

5. The method of claim 1 wherein said zygosity is measured using a DNA fingerprinting technique.

6. A method for determining the presence of a partial Williams syndrome profile, said method comprising determining the presence of a complete deletion of LIM-kinase 1 (LIMK1) and a deletion of at least a 3' terminal region of elastin (ELN) on one chromosome, wherein said presence of a complete deletion of LIMK1 and a deletion of at least a 3' terminal region of ELN, said deletion of a 3' terminal region of ELN comprising a region from exon 28 through the stop codon of ELN, on one chromosome and further wherein no more than about 100 kb 3' to LIMK1 is deleted on said chromosome is indicative of the presence of a partial Williams syndrome profile.

7. The method of claim 6 wherein said method comprises in situ hybridization.

8. The method of claim 6 wherein said method comprises fluorescent in situ hybridization.

9. The method of claim 6 wherein said method comprises a polymerase chain reaction.

10. The method of claim 6 wherein said method comprises a DNA fingerprinting technique.

11. A method for distinguishing whether an individual has supravalvular aortic stenosis (SVAS), partial Williams syndrome profile or Williams syndrome (WS), said method comprising analyzing an individual's chromosomes for deletions of portions of chromosome 7 wherein a deletion of elastin (ELN) but not LIM-kinase 1 (LIMK1) is indicative of SVAS, a deletion of ELN and LIMK1 but no more than about 100 kb 3' to LIMK1 is indicative of partial Williams syndrome, and a deletion of ELN, LIMK1 and greater than 300 kb 3' of LIMK1 is indicative of WS.

12. The method of claim 11 wherein said analyzing comprises in situ hybridization.

13. The method of claim 11 wherein said analyzing comprises fluorescent in situ hybridization.

14. The method of claim 11 wherein said analyzing comprises a polymerase chain reaction.

15. The method of claim 11 wherein said analyzing comprises a DNA fingerprinting technique.

* * * * *